(12) United States Patent
Price et al.

(10) Patent No.: US 10,646,374 B2
(45) Date of Patent: May 12, 2020

(54) APPARATUS AND METHOD TO FORM ENTRY BLEB FOR SUBRETINAL DELIVERY OF THERAPEUTIC AGENT

(71) Applicant: ORBIT BIOMEDICAL LIMITED, London (GB)

(72) Inventors: Daniel W. Price, Loveland, OH (US); Brendan J. Oberkircher, Cincinnati, OH (US); Daniel J. Prenger, Loveland, OH (US); Geoffrey King, Cincinnati, OH (US); Thomas E. Meyer, Cincinnati, OH (US); Benjamin L. Ko, Cincinnati, OH (US)

(73) Assignee: ORBIT BIOMEDICAL LIMITED, London (GB)

(*) Notice: Subject to any disclaimer, the term of this patent is extended or adjusted under 35 U.S.C. 154(b) by 0 days.

(21) Appl. No.: 15/609,386

(22) Filed: May 31, 2017

(65) Prior Publication Data

US 2017/0360607 A1    Dec. 21, 2017

Related U.S. Application Data

(60) Provisional application No. 62/351,611, filed on Jun. 17, 2016.

(51) Int. Cl.
*A61F 9/007* (2006.01)
*A61F 9/00* (2006.01)
(Continued)

(52) U.S. Cl.
CPC ........ *A61F 9/00736* (2013.01); *A61F 9/0008* (2013.01); *A61B 2017/3405* (2013.01);
(Continued)

(58) Field of Classification Search
CPC .... A61F 9/007; A61F 9/00735; A61F 9/0008; A61F 9/00; A61F 9/0017; A61B 17/3403;
(Continued)

(56) References Cited

U.S. PATENT DOCUMENTS

| 5,709,661 A * | 1/1998 | Van Egmond | ..... A61B 1/00147 33/512 |
| 6,171,276 B1 * | 1/2001 | Lippe | ..... A61M 5/20 128/DIG. 1 |

(Continued)

FOREIGN PATENT DOCUMENTS

WO    WO 2017/042584 A1    3/2017

OTHER PUBLICATIONS

International Search Report and Written Opinion dated Sep. 14, 2017 for Application No. PCT/US2017/037361, 17 pgs.
U.S. Appl. No. 62/351,611, filed Jun. 16, 2016.

*Primary Examiner* — Brandy S Lee
*Assistant Examiner* — Hong-Van N Trinh
(74) *Attorney, Agent, or Firm* — Frost Brown Todd LLC

(57) ABSTRACT

An apparatus includes an injector, a first fluid conduit, a second fluid line, and a control module. The injector includes a body, a flexible cannula, a flexible needle, and a sensor. The needle is configured to translate relative to the cannula. The sensor is operable to detect a position of the needle relative to the cannula. The first and second fluid lines are coupled with the needle. The control module is in communication with the sensor, with the first fluid conduit, and with the second fluid conduit. The control module is configured to provide delivery of a first fluid through the first conduit to the needle based on a signal from the sensor. The control module is further configured to provide delivery of a second fluid through the second conduit to the needle.

19 Claims, 35 Drawing Sheets

(51) Int. Cl.
   *A61B 17/34*   (2006.01)
   *A61M 5/20*   (2006.01)
   *A61M 5/24*   (2006.01)

(52) U.S. Cl.
   CPC ............... *A61F 9/007* (2013.01); *A61M 5/20* (2013.01); *A61M 5/24* (2013.01)

(58) Field of Classification Search
   CPC .......... A61B 2017/3405; A61B 5/6849; A61B 5/14503; A61B 5/1455; A61B 2562/0223; A61B 2017/00022; A61B 5/15109; A61M 3/02; A61M 2005/1787; A61M 5/19; A61M 1/0058; A61M 1/0062; A61M 1/0064; A61M 2205/01; A61M 2005/14252; A61M 2205/3306; A61M 5/158; A61M 2205/14; A61M 2205/6063; A61M 2205/583; A61M 5/20
   See application file for complete search history.

(56) References Cited

U.S. PATENT DOCUMENTS

| | | |
|---|---|---|
| 6,368,315 B1 | 4/2002 | Gillis et al. |
| 6,824,532 B2 | 11/2004 | Gillis et al. |
| 7,189,245 B2 | 3/2007 | Kaplan |
| 7,207,980 B2 | 4/2007 | Christian et al. |
| 7,413,734 B2 | 8/2008 | Mistry et al. |
| 8,197,435 B2 | 6/2012 | Prausnitz et al. |
| 8,425,473 B2 | 4/2013 | Ho et al. |
| 2005/0143363 A1 | 6/2005 | de Juan et al. |
| 2006/0257835 A1* | 11/2006 | Wallaker ................ G09B 23/28 434/262 |
| 2008/0058704 A1 | 3/2008 | Hee et al. |
| 2012/0191064 A1 | 7/2012 | Conston et al. |
| 2012/0271272 A1 | 10/2012 | Hammack et al. |
| 2013/0216623 A1 | 8/2013 | Yamamoto et al. |
| 2013/0245600 A1 | 9/2013 | Yamamoto et al. |
| 2015/0164687 A1* | 6/2015 | Kashani ................ A61M 5/32 604/506 |
| 2015/0209180 A1 | 7/2015 | Prausnitz et al. |
| 2015/0223977 A1 | 8/2015 | Oberkircher et al. |
| 2015/0258120 A1 | 9/2015 | Zarnitsyn et al. |
| 2015/0351958 A1 | 12/2015 | Contiliano et al. |
| 2015/0351959 A1 | 12/2015 | Clem et al. |
| 2016/0074211 A1 | 3/2016 | Ko et al. |
| 2016/0074212 A1 | 3/2016 | Price et al. |
| 2016/0074217 A1 | 3/2016 | Price et al. |
| 2016/0081849 A1 | 3/2016 | Tsai et al. |
| 2017/0095369 A1 | 4/2017 | Andino et al. |
| 2017/0252209 A1* | 9/2017 | Gooi ....................... A61M 5/19 |
| 2017/0258988 A1 | 9/2017 | Meyer et al. |
| 2017/0333416 A1 | 11/2017 | Zarnitsyn et al. |
| 2017/0360605 A1 | 12/2017 | Oberkircher et al. |
| 2017/0360606 A1 | 12/2017 | Price et al. |
| 2018/0042765 A1 | 2/2018 | Noronha et al. |

\* cited by examiner

US 10,646,374 B2

APPARATUS AND METHOD TO FORM ENTRY BLEB FOR SUBRETINAL DELIVERY OF THERAPEUTIC AGENT

PRIORITY

This application claims priority to U.S. Provisional Patent Application No. 62/351,611, entitled "Entry Bleb Formation During Choroidal Penetration," filed Jun. 17, 2016, the disclosure of which is incorporated by reference herein.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
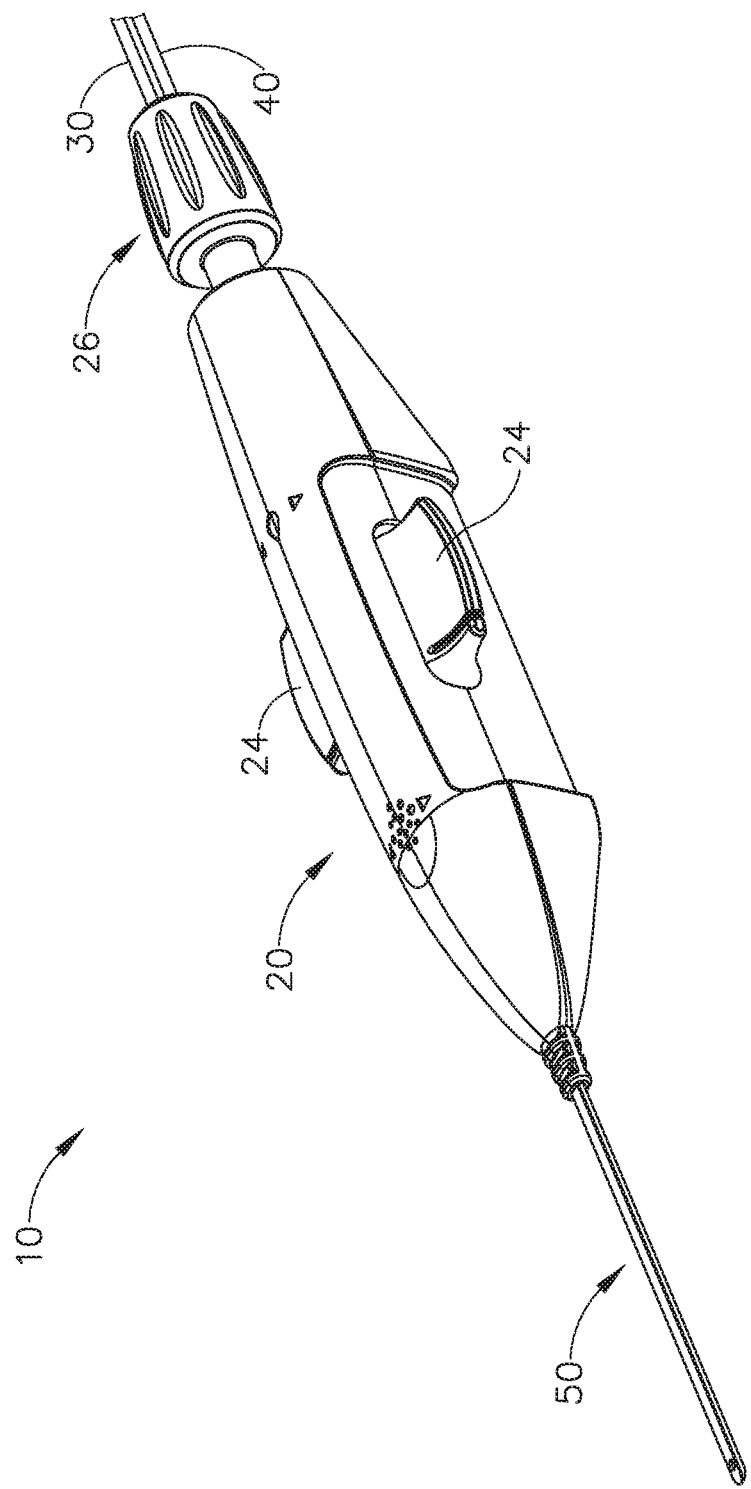
FIG. 1 depicts a perspective view of an exemplary instrument for subretinal administration of a therapeutic agent from a suprachoroidal approach.
Figure 2:
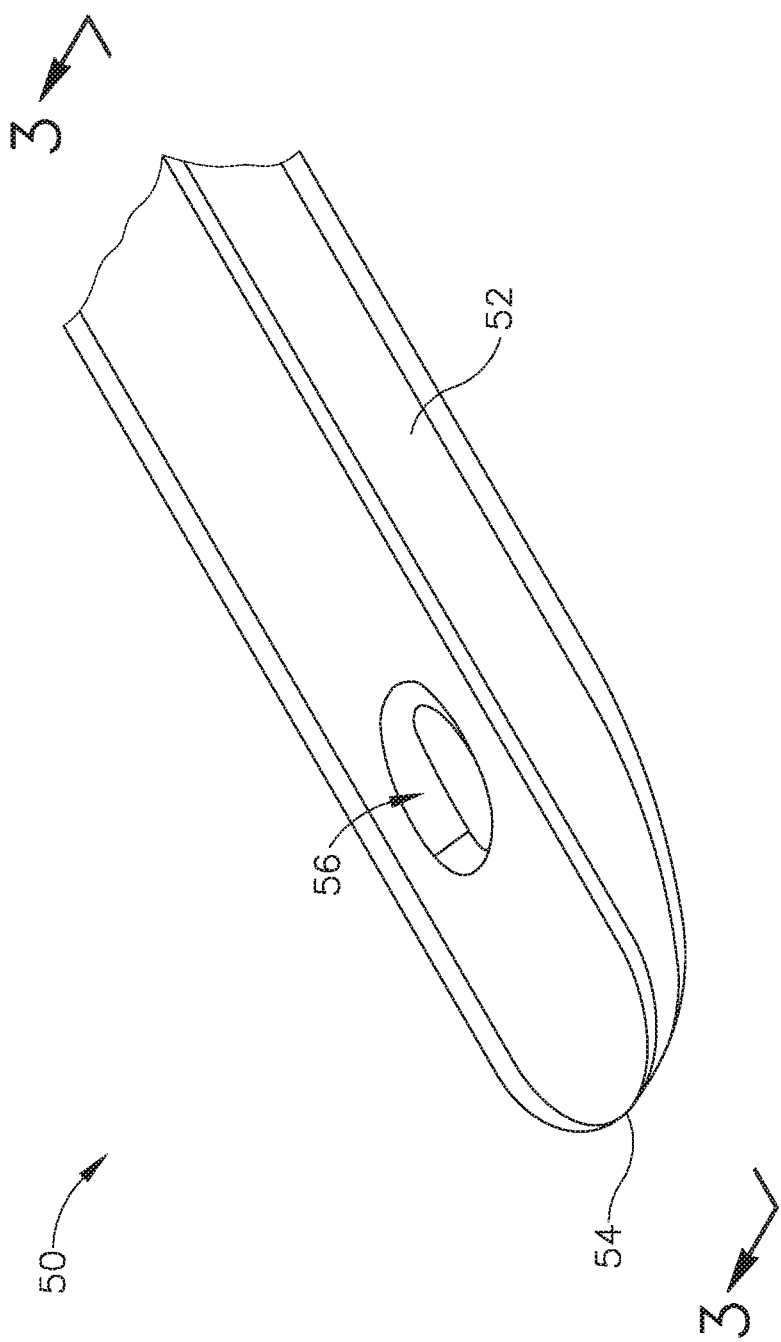
FIG. 2 depicts a perspective view of the distal end of an exemplary cannula that may be incorporated into the instrument of FIG. 1.

The drawings are not intended to be limiting in any way, and it is contemplated that various embodiments of the technology may be carried out in a variety of other ways, including those not necessarily depicted in the drawings.

The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument for Subretinal Administration of Therapeutic Agent

FIG. 1 shows an exemplary instrument (10) that is configured for use in a procedure for the subretinal administration of a therapeutic agent to an eye of a patient from a suprachoroidal approach. Instrument (10) comprises a body (20) and a flexible cannula (50) extending distally from body (20). Cannula (50) of the present example has a generally rectangular cross section, though any other suitable cross-sectional profile (e.g., elliptical, etc.) may be used. Cannula (50) is generally configured to support a needle (100) that is slidable within cannula (50), as will be described in greater detail below.

In the present example, cannula (50) comprises a flexible material such as Polyether block amide (PEBA), which may be manufactured under the trade name PEBAX. Of course, any other suitable material or combination of materials may be used. Also in the present example, cannula (50) has a cross-sectional profile dimension of approximately 2.0 mm by 0.8 mm, with a length of approximately 80 mm. Alternatively, any other suitable dimensions may be used. As will be described in greater detail below, cannula (50) is flexible enough to conform to specific structures and contours of the patient's eye, yet cannula (50) has sufficient column strength to permit advancement of cannula (50) between the sclera and choroid of patient's eye without buckling. By way of example only, cannula (50) may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein.

Figure 3A:
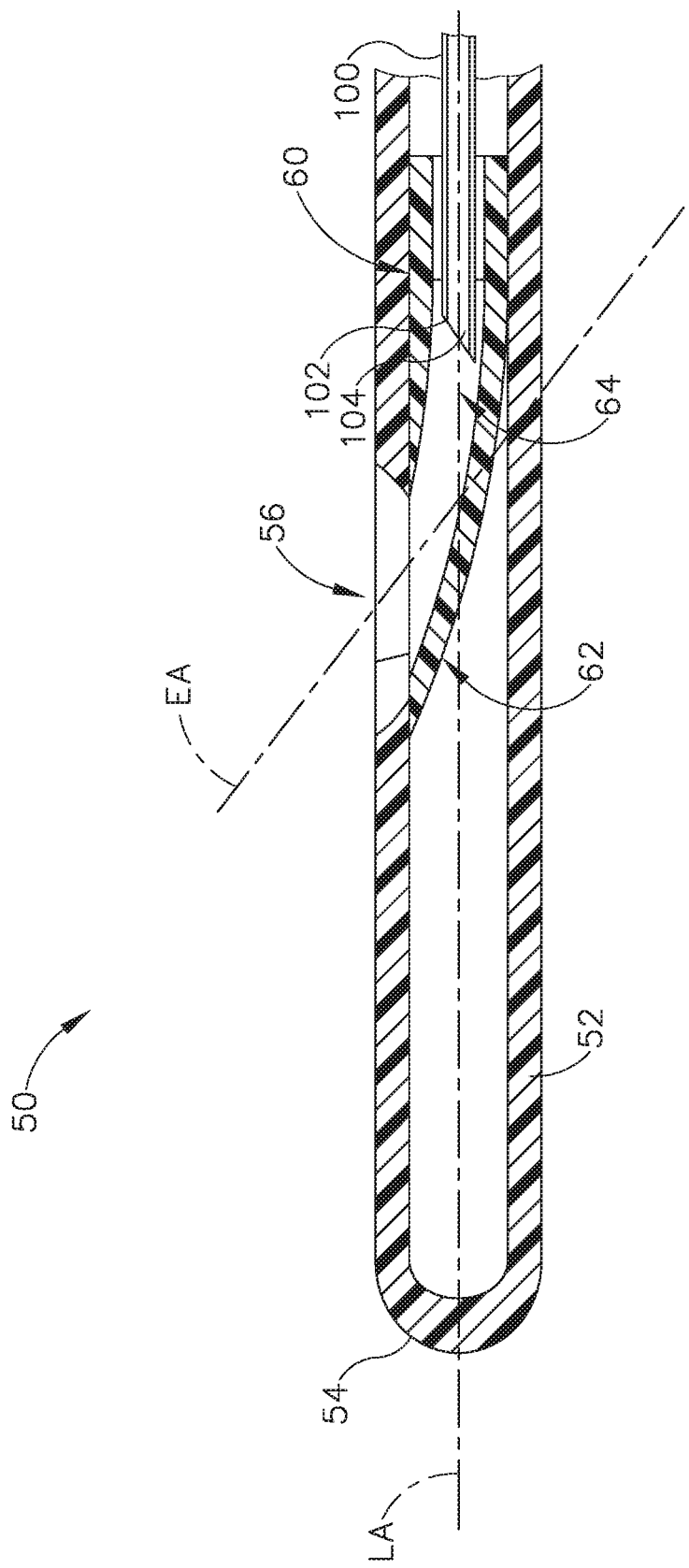
FIG. 3A depicts a cross-sectional side view of the cannula of FIG. 2, with the cross-section taken along line 3-3 of FIG. 2, with a needle in a first longitudinal position.
Figure 3B:
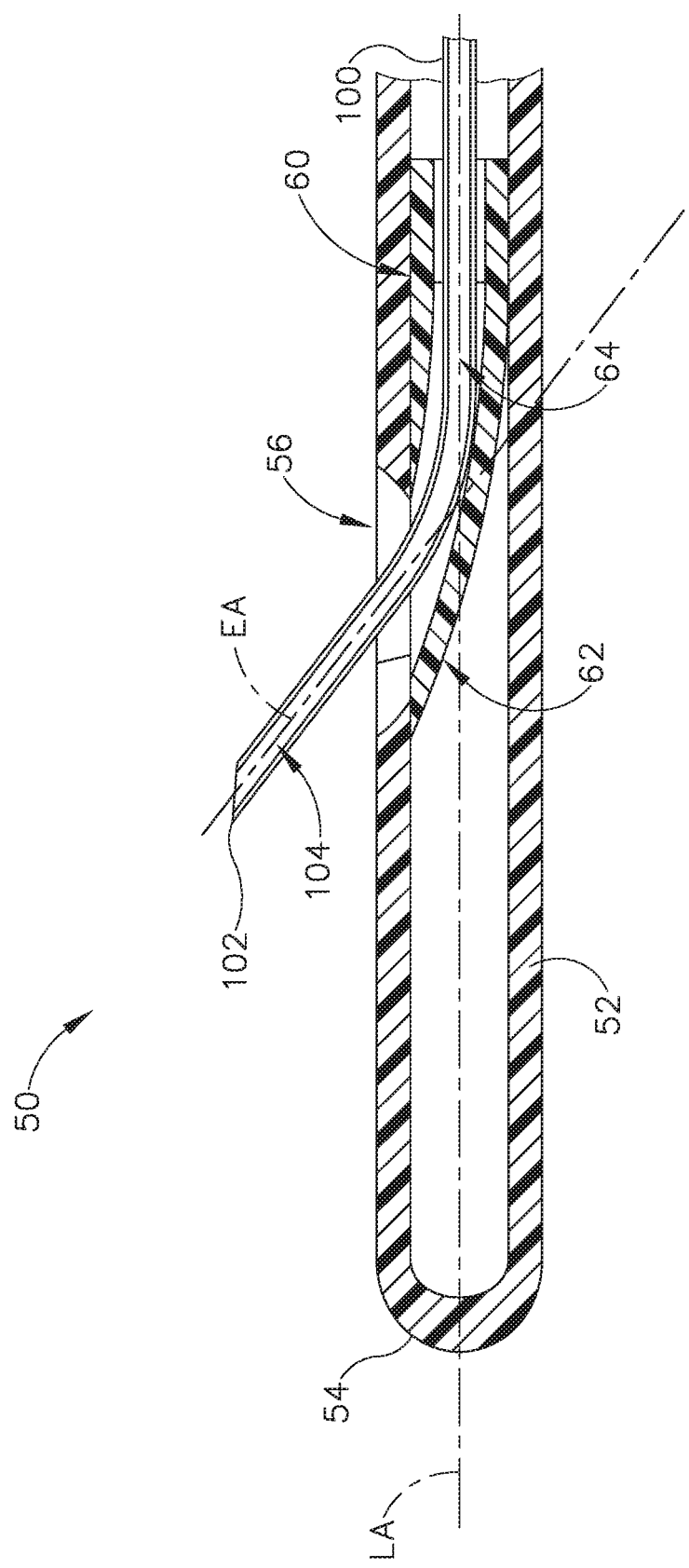
FIG. 3B depicts a cross-sectional side view of the cannula of FIG. 2, with the cross-section taken along line 3-3 of FIG. 2, with the needle in a second longitudinal position.

As can be seen in FIGS. 2-3B and 6, cannula (50) comprises a body (52), a closed distal end (54), and a lateral opening (56) that is located proximal to distal end (54). In the present example, distal end (54) has a rounded configuration. It should be understood that distal end (54) may have any suitable kind of curvature. It should also be understood that distal end (54) may have any other suitable kind of configuration (e.g., beveled, etc.). In the present example, distal end (54) is configured to provide separation between the sclera and choroid layers to enable cannula (50) to be advanced between such layers while not inflicting trauma to the sclera or choroid layers. Also in the present example, the region of body (52) that defines lateral opening (56) is beveled, as best seen in FIGS. 3A-3B. Alternatively, the edge of lateral opening (56) may have any other suitable configuration.

As best seen in FIGS. 3A-3B, a needle guide (60) is disposed within the hollow interior of cannula (50). By way of example only, needle guide (60) may be secured within cannula (50) by a press or interference fit, by adhesives, by mechanical locking mechanisms, and/or in any other suitable fashion. Needle guide (60) includes a curved distal end (62) that leads to lateral opening (56) of cannula (50), such that a lumen (64) of needle guide (60) distally terminates at lateral opening (56). The portion of needle guide (60) that is proximal to distal end (62) is substantially straight. Needle guide (60) may be formed of plastic, stainless steel, and/or any other suitable biocompatible material(s).

Needle (100) of the present example has a sharp distal tip (102) and defines a lumen (104). Distal tip (102) of the present example has a lancet configuration. In some other versions, distal tip (102) has a tri-bevel configuration or any other configuration as described in U.S. Pub. No. 2015/0223977, entitled "Method and Apparatus for Subretinal Administration of Therapeutic Agent," published Aug. 13, 2015, the disclosure of which is incorporated by reference herein. Still other suitable forms that distal tip (102) may take will be apparent to those of ordinary skill in the art in view of the teachings herein. Needle (100) of the present example comprises a stainless steel hypodermic needle that is sized to deliver the therapeutic agent while being small enough to minimize incidental trauma as needle (100) penetrates tissue structures of the patient's eye, as will be described in greater detail below. While stainless steel is used in the present example, it should be understood that any other suitable material(s) may be used, including but not limited to nitinol, etc.

By way of example only, needle (100) may be 35 gauge with a 100 μm inner diameter, although other suitable sizes may be used. For instance, the outer diameter of needle (100) may fall within the range of 27 gauge to 45 gauge; or more particularly within the range of 30 gauge to 42 gauge; or more particularly within the range of 32 gauge to 39 gauge. As another merely illustrative example, the inner diameter of needle (100) may fall within the range of approximately 50 μm to approximately 200 μm; or more particularly within the range of approximately 50 μm to approximately 150 μm; or more particularly within the range of approximately 75 μm to approximately 125 μm.

Needle (100) is slidably disposed within lumen (64) of needle guide (60). Needle guide (60) is generally configured to direct needle (100) upwardly along an exit axis (EA) that is obliquely oriented relative to the longitudinal axis (LA) of cannula (50) through lateral opening (56) of cannula (50). This is shown in the sequence depicted in FIGS. 3A-3B, in which FIG. 3A shows needle (100) in a proximal position (where distal tip (102) of needle (100) is fully contained in lumen (64) of needle guide (60)); and FIG. 3B shows needle (100) in a distal position (where distal tip (102) of needle (100) is outside of needle guide (60)). While needle (100) is flexible, needle (100) of the present example is resiliently biased to assume a straight configuration. Thus, as shown in FIG. 3B, the portion of needle (100) that extends outside of cannula (50) and needle guide (60) is substantially straight, extending along exit axis (EA). In particular, at least a substantial length of the portion of needle (100) that extends outside of cannula (50) and needle guide (60) is coaxially aligned with exit axis (EA).

It should be understood that the depiction of exit axis (EA) in FIGS. 3A-3B may be somewhat exaggerated, for illustrative purposes only. In some versions, curved distal end (62) is configured to direct needle (100) along an exit axis (EA) that extends distally from cannula (50) at an angle of approximately 7° to approximately 9° relative to the longitudinal axis (LA) of cannula (50). It should be understood that such an angle may be desirable to deflect needle (100) in a direction to ensure penetration of needle into the choroid and to minimize the possibility of needle (100) continuing beneath the choroid through the suprachoroidal space (as opposed to penetrating through the choroid) and the possibility of retinal perforation. By way of further example only, curved distal portion (88) may urge needle (100) to exit cannula (50) along an exit axis (EA) that is oriented at an angle within the range of approximately 5° to approximately 30° relative to the longitudinal axis (LA) of cannula (50); or more particularly within the range of approximately 5° to approximately 20° relative to the longitudinal axis (LA) of cannula (50); or more particularly within the range of approximately 5° to approximately 10° relative to the longitudinal axis (LA) of cannula (50).

As shown in FIG. 1, instrument (10) of the present example further comprises an actuation knob (26) located at the proximal end of body (20). Actuation knob (26) is rotatable relative to body (20) to thereby selectively translate needle (100) longitudinally relative to cannula (50). In particular, actuation knob (26) is rotatable in a first angular direction to drive needle (100) distally relative to cannula (50); and in a second angular direction to drive needle (100) proximally relative to cannula (50). By way of example only, instrument (10) may provide such functionality through knob (26) in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein. Alternatively, any other suitable kind of actuation feature(s) may be used to drive needle (100) longitudinally relative to cannula (50).

In the present example, knob (26) is rotatable through a complete range of motion that corresponds to advancement of needle (100) to a position relative to cannula (50) to a predetermined amount of penetration within an eye of a patient. In other words, instrument (10) is configured such that an operator rotates knob (26) until knob (26) can no longer rotate, or until knob (26) begins to slip or "freewheel" in a clutch assembly, to properly position needle (100) within an eye of a patient. In some examples, the predetermined amount of advancement of needle (100) relative to cannula (50) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm.

In addition or in the alternative, instrument (10) may be equipped with certain tactile feedback features to indicate to an operator when needle (100) has been advanced to certain predetermined distances relative to cannula (50). Accordingly, an operator may determine the desired depth of penetration of needle (100) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

As also shown in FIG. 1, a pair of supply tubes (30, 40) extend proximally from actuator knob (26). In the present example, first supply tube (30) is configured to couple with a source of bleb fluid (340) (e.g., BSS); while second supply tube (40) is configured to couple with a source of therapeutic agent (341). It should be understood that each fluid supply tube (30, 40) may include a conventional luer feature and/or other structures permitting fluid supply tubes (30, 40) to be coupled with respective fluid sources. Fluid supply tubes (30, 40) lead to a valve assembly that includes actuation arms (24). Actuation arms (24) are pivotable to selectively change the state of the valve assembly. Based on the pivotal position of actuation arms (24), the valve assembly is operable to selectively pinch or otherwise open/close the supply of fluid from fluid supply tubes (30, 40) to lumen (104) of needle (100). Thus, actuation arms (24) are operable to selectively control the delivery of bleb fluid (340) and therapeutic agent (341) via needle (100). By way of example only, the valve assembly may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein. Other suitable features and configurations that may be used to control fluid delivery via needle (100) will be apparent to those of ordinary skill in the art in view of the teachings herein.

It should be understood that the features and operability of instrument (10) may be varied in numerous ways. In addition, instrument (10) may be modified in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein. Other suitable modifications will be apparent to those of ordinary skill in the art in view of the teachings herein.

II. Exemplary Procedure for Subretinal Administration of Therapeutic Agent

FIGS. 4A-5C show an exemplary procedure for subretinal delivery of therapeutic agent from a suprachoroidal approach using instrument (10) described above. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 4A:
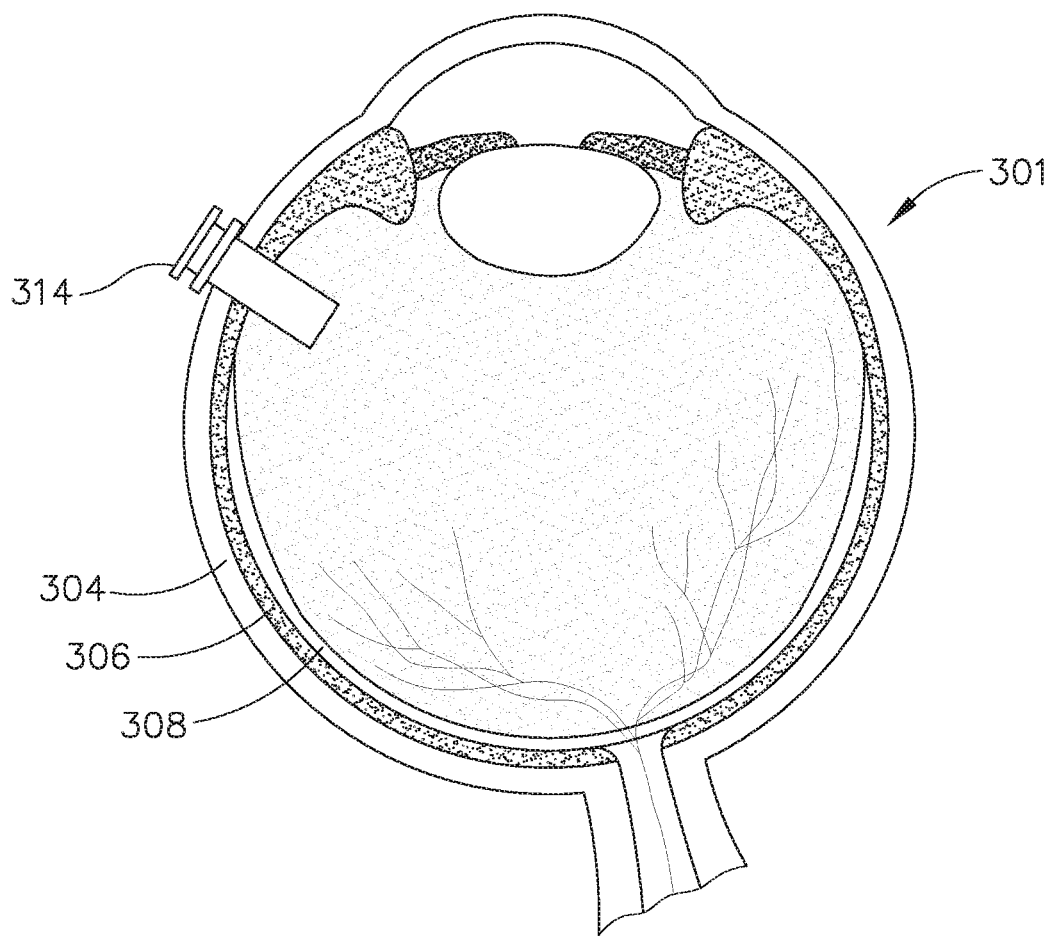
FIG. 4A depicts a cross-sectional view of an eye of a patient, with a chandelier installed in the eye.

In the present example, the procedure begins by an operator immobilizing tissue surrounding a patient's eye (301) (e.g., the eyelids) using a speculum, and/or any other instrument suitable for immobilization. While immobilization described herein with reference to tissue surrounding eye (301), it should be understood that eye (301) itself may remain free to move. Once the tissue surrounding eye (301) has been immobilized, an eye chandelier port (314) is inserted into eye (301), as shown in FIG. 4A, to provide intraocular illumination when the interior of eye (301) is viewed through the pupil. In the present example, eye chandelier port (314) is positioned in the inferior medial quadrant such that a superior temporal quadrant sclerotomy may be performed. Eye chandelier port (314) is positioned to direct light onto the interior of eye (301) to illuminate at least a portion of the retina (e.g., including at least a portion of the macula). As will be understood, such illumination corresponds to an area of eye (301) that is being targeted for delivery of therapeutic agent.

In the present example, only chandelier port (314) is inserted at the stage shown in FIG. 4A, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. Although FIG. 4A shows a particular positioning of eye chandelier port (314), it should be understood that eye chandelier port (314) may have any other positioning as will be apparent to those of ordinary skill in the art in view of the teachings herein.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. A template may then be used to mark eye (301), as described in U.S.

Figure 4B:
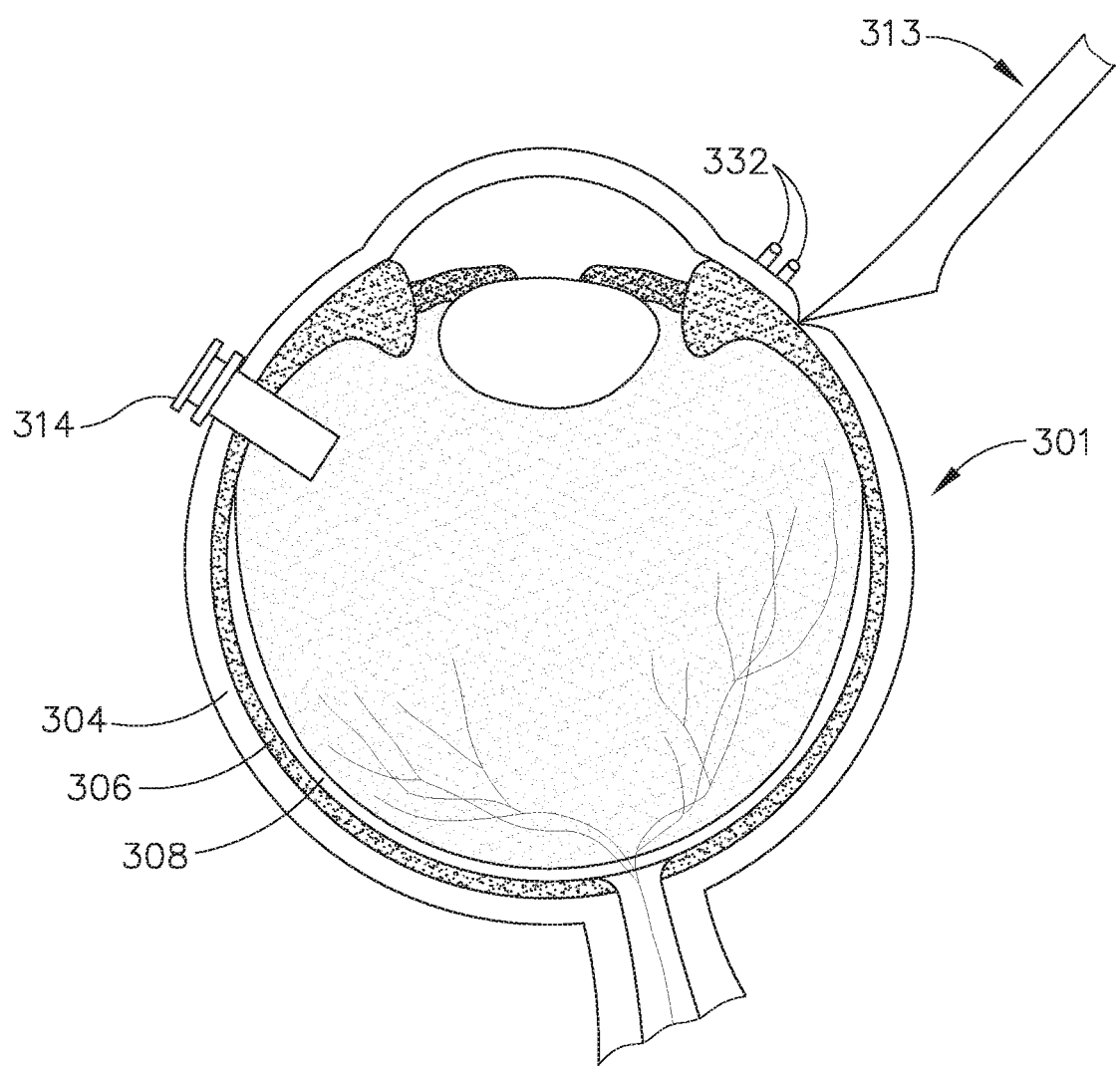
FIG. 4B depicts a cross-sectional view of the eye of FIG. 4A, with a suture loop attached to the eye, and with a sclerotomy being performed.

Pub. No. 2015/0223977, entitled "Method and Apparatus for Subretinal Administration of Therapeutic Agent," published Aug. 13, 2015, the disclosure of which is incorporated by reference herein. An operator may then use a visual guide created using the template to attach a suture loop assembly (332) and to perform a sclerotomy, as shown in FIG. 4B, using a conventional scalpel (313) or other suitable cutting instrument. The sclerotomy procedure forms a small incision through sclera (304) of eye (301). The sclerotomy is performed with particular care to avoid penetration of the choroid (306). Thus, the sclerotomy procedure provides access to the space between sclera (304) and choroid (306). Once the incision is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 4C:
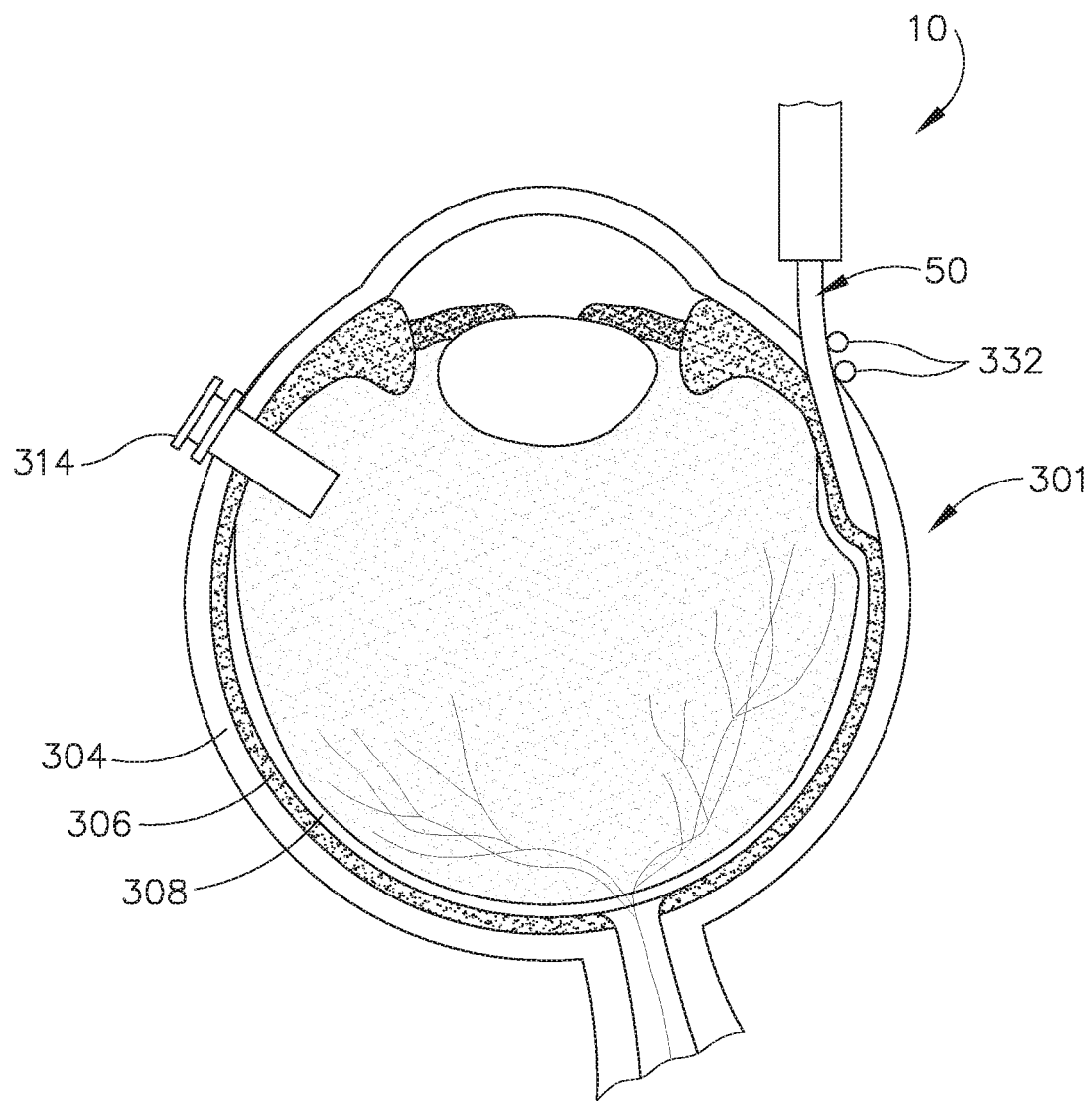
FIG. 4C depicts a cross-sectional view of the eye of FIG. 4A, with the instrument of FIG. 1 being inserted through the sclerotomy opening and in between the sclera and choroid of the eye.

With the sclerotomy procedure performed, an operator may insert cannula (50) of instrument (10) through incision (316) and into the space between sclera (304) and choroid (306). As can be seen in FIG. 4C, cannula (50) is directed through suture loop assembly (332) and into the incision. Suture loop assembly (332) may stabilize cannula (50) during insertion. Additionally, suture loop assembly (332) maintains cannula (50) in a generally tangential orientation relative to the incision. Such tangential orientation may reduce trauma as cannula (50) is guided through the incision. As cannula (50) is inserted into the incision through suture loop assembly (332), an operator may use forceps or other instruments to further guide cannula (50) along an atraumatic path. Of course, use of forceps or other instruments is merely optional, and may be omitted in some examples.

Although not shown, it should be understood that in some examples cannula (50) may include one or more markers on the surface of cannula (50) to indicate various depths of insertion. While merely optional, such markers may be desirable to aid an operator in identifying the proper depth of insertion as cannula (50) is guided along an atraumatic path. For instance, the operator may visually observe the position of such markers in relation to suture loop assembly (332) and/or in relation to the incision in the sclera (304) as an indication of the depth to which cannula (50) is inserted in eye (301). By way of example only, one such marker may correspond to an approximately 6 mm depth of insertion of cannula (50).

Figure 4D:
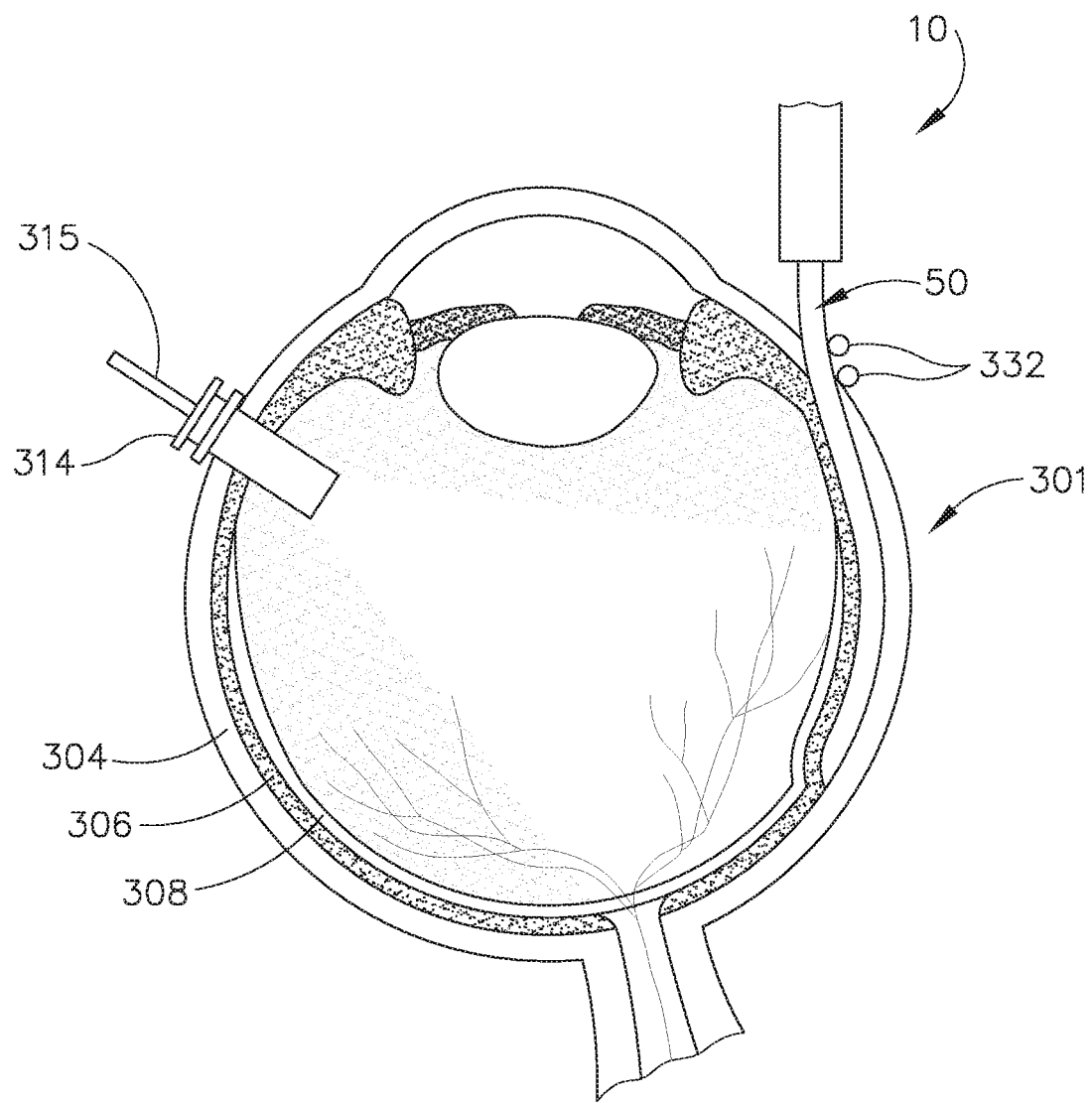
FIG. 4D depicts a cross-sectional view of the eye of FIG. 4A, with the instrument of FIG. 1 under direct visualization at the back of the eye, between the sclera and choroid.

As shown in FIG. 4D, once cannula (50) is at least partially inserted into eye (301), an operator may insert an optical fiber (315) into eye chandelier port (314) if the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (50) may optionally be made at this point to ensure proper positioning relative to the area of geographic atrophy of retina (308). In some instances, the operator may wish to rotate the eye (301), such as by pulling on suture loop assembly (332), to direct the pupil of the eye (301) toward the operator in order to optimize visualization of the interior of the eye (301) via the pupil.

FIGS. 4C-4D show cannula (50) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. By way of example only, the operator may rely on direct visualization through a microscope directed through the pupil of eye (301) as cannula (50) is being advanced through the range of motion shown in FIGS. 4C-4D, with illumination provided through fiber (315) and port (314). Cannula (50) may be at least partially visible through a retina (308) and choroid (306) of eye (301). Visual tracking may be enhanced in versions where an optical fiber is used to emit visible light through the distal end of cannula (50).

Figure 4E:
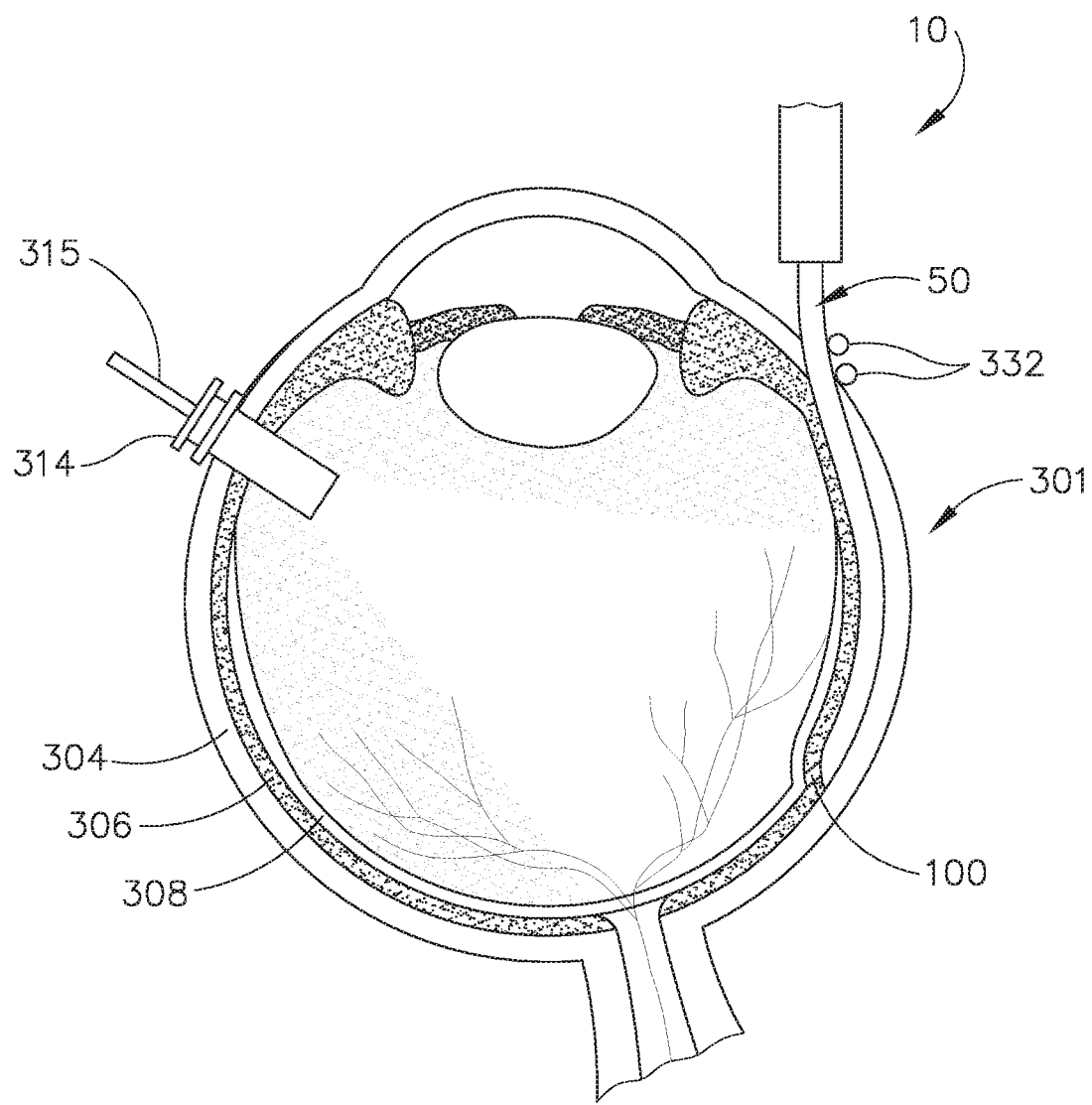
FIG. 4E depicts a cross-sectional view of the eye of FIG. 4A, with the needle of the instrument of FIG. 1 being advanced under direct visualization at the back of the eye, pressing against the outer surface of the choroid causing the choroid to "tent"
Figure 5A:
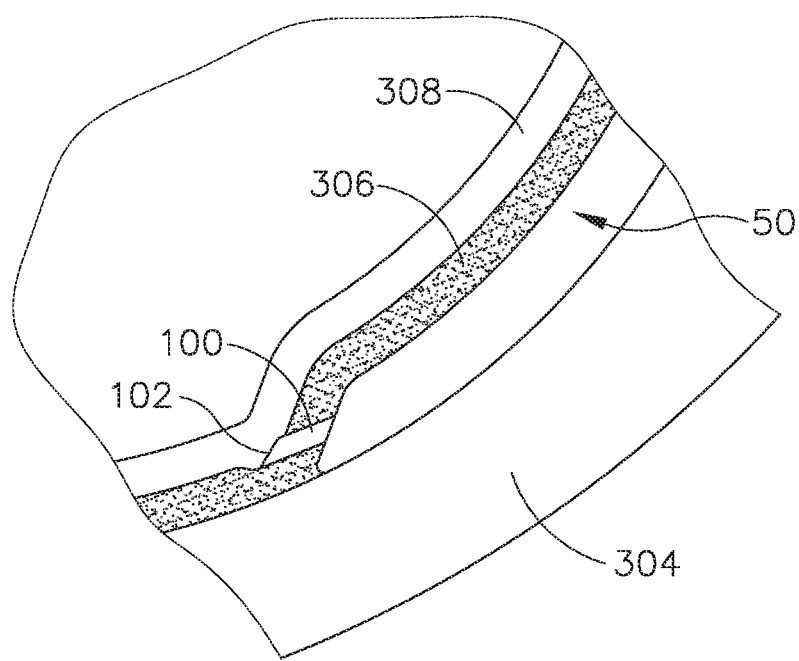
FIG. 5A depicts a detailed cross-sectional view of the eye of FIG. 4A depicted in the state shown in FIG. 4E.

Once cannula (50) has been advanced to the delivery site as shown in FIG. 4D, an operator may advance needle (100) of instrument (10) as described above by actuating knob (26). As can be seen in FIGS. 4E and 5A, needle (100) is advanced relative to cannula (50) such that needle (100) pierces through choroid (306) without penetrating retina (308). Immediately prior to penetrating choroid (306), needle (100) may appear under direct visualization as "tenting" the surface of choroid (306). In other words, needle (100) may deform choroid (306) by pushing upwardly on choroid (306), providing an appearance similar to a tent pole deforming the roof of a tent. Such a visual phenomenon may be used by an operator to identify whether choroid (306) is about to be pierced and the location of any eventual piercing. The particular amount of needle (100) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (100) advancement may be between approximately 0.25 mm and approximately 10 mm; or more particularly between approximately 2 mm and approximately 6 mm.

Figure 4F:
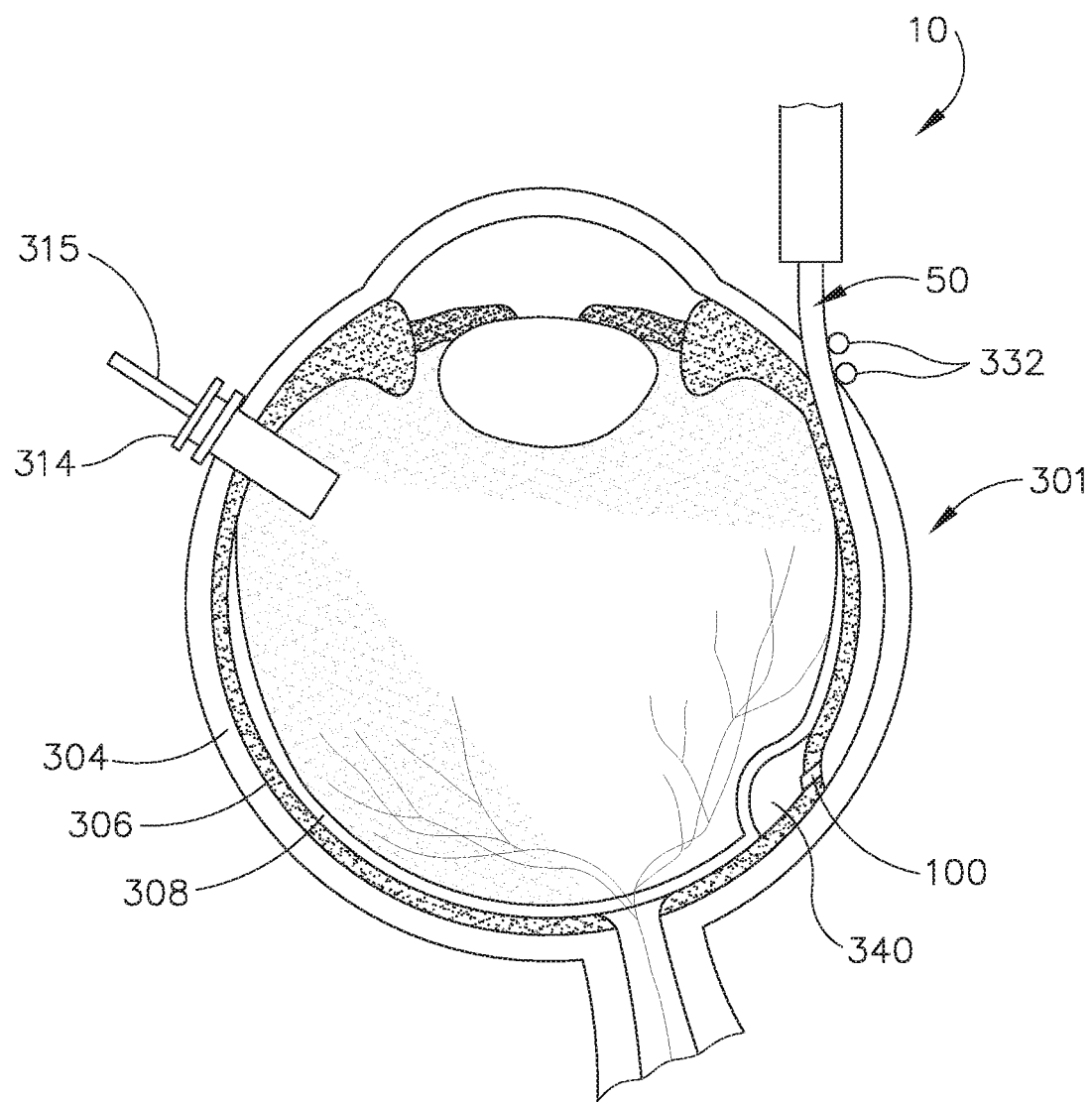
FIG. 4F depicts a cross-sectional view of the eye of FIG. 4A, with the needle dispensing a leading bleb under direct visualization at the back of the eye, the needle between the sclera and choroid, and the leading bleb in the subretinal space between the choroid and a retina.
Figure 5B:
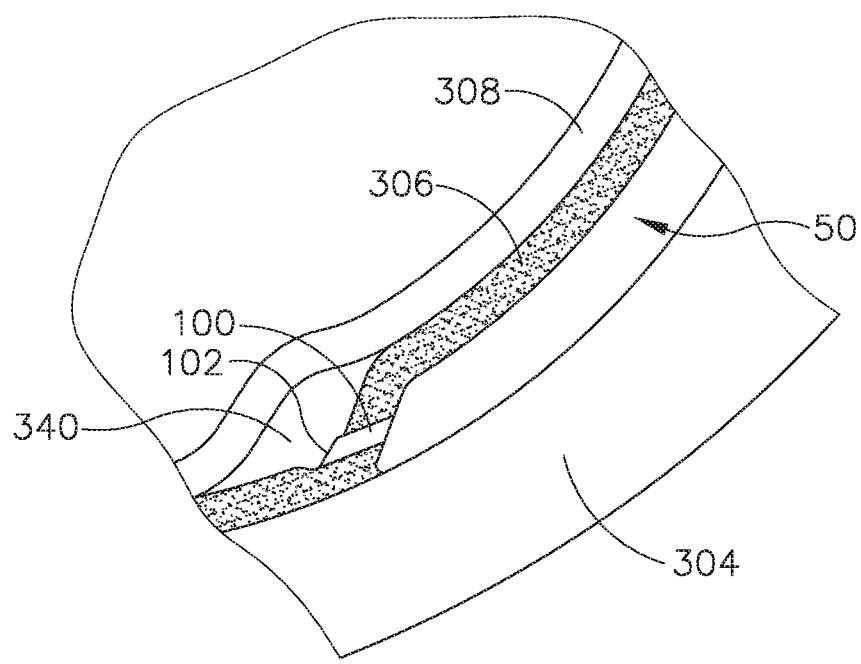
FIG. 5B depicts a detailed cross-sectional view of the eye of FIG. 4A depicted in the state shown in FIG. 4F.

In the present example, after the operator has confirmed that needle (100) has been properly advanced by visualizing the tenting effect described above, the operator infuses a balanced salt solution (BSS) or other similar solution as needle (100) is advanced relative to cannula (50). Such a BSS may form a leading bleb (340) ahead of needle (100) as needle (100) is advanced through choroid (306). Leading bleb (340) may be desirable for two reasons. First, as shown in FIGS. 4F and 5B, leading bleb (340) may provide a further visual indicator to an operator to indicate when needle (100) is properly positioned at the delivery site. Second, leading bleb (340) may provide a barrier between needle (100) and retina (308) once needle (100) has penetrated choroid (306). Such a barrier may push the retinal wall outwardly, thereby minimizing the risk of retinal perforation as needle (100) is advanced to the delivery site. In some versions, a foot pedal is actuated in order to drive leading bleb (340) out from needle (100). Alternatively, other suitable features that may be used to drive leading bleb (340) out from needle (100) will be apparent to those of ordinary skill in the art in view of the teachings herein.

Once the operator visualizes leading bleb (340), the operator may cease infusion of BSS, leaving a pocket of fluid as can be seen in FIGS. 4F and 5B. Next, a therapeutic agent (341) may be infused by actuating a syringe or other fluid delivery device as described in various references cited herein. The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, tissue plasminogen activators, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. In addition to, or as an alternative to, being used to deliver a therapeutic agent (341), instrument (10) and variations thereof may be used to provide drainage and/or perform other operations.

Figure 4G:
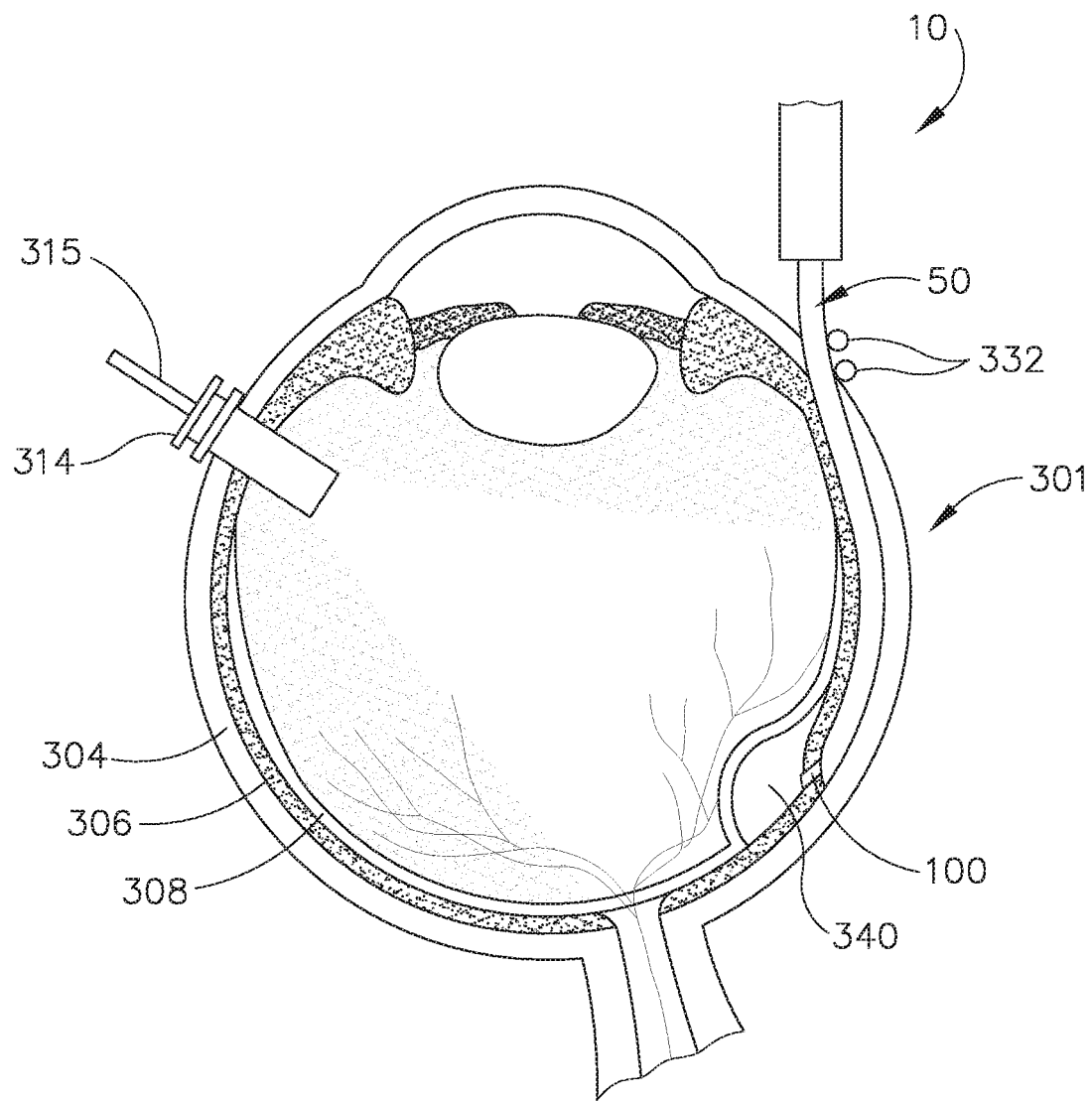
FIG. 4G depicts a cross-sectional view of the eye of FIG. 4A, with the needle dispensing a therapeutic agent to the eye at the back of the eye, between the sclera and choroid.
Figure 5C:
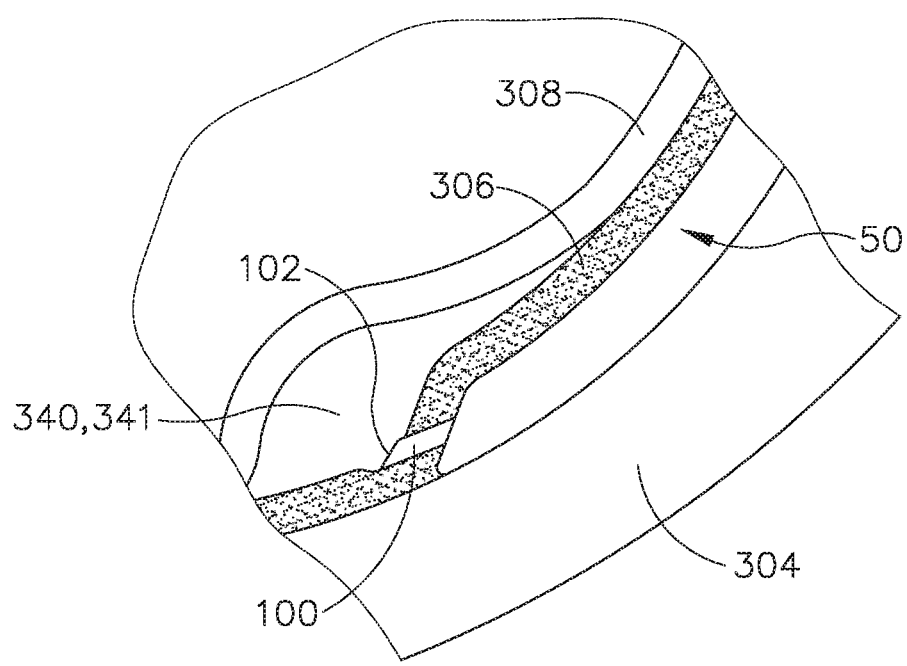
FIG. 5C depicts a detailed cross-sectional view of the eye of FIG. 4A depicted in the state shown in FIG. 4G.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (100). Alternatively, other suitable features that may be used to drive agent (341) out from needle (100) will be apparent to those of ordinary skill in the art in view of the teachings herein. Delivery of therapeutic agent (341) may be visualized by an expansion of the pocket of fluid as can be seen in FIGS. 4G and 5C. As shown, therapeutic agent (341) essentially mixes with the fluid of leading bleb (340) as therapeutic agent (341) is injected into the suprachoroidal, subretinal space.

Once delivery is complete, needle (100) may be retracted by rotating knob (26) in a direction opposite to that used to advance needle (100); and cannula (50) may then be withdrawn from eye (301). It should be understood that because of the size of needle (100), the site where needle (100) penetrated through choroid (306) is self-sealing, such that no further steps need be taken to seal the delivery site through choroid (306). Suture loop assembly (332) and chandelier (314) may be removed, and the incision in the sclera (304) may be closed using any suitable conventional techniques.

As noted above, the foregoing procedure may be carried out to treat a patient having macular degeneration. In some such instances, the therapeutic agent (341) that is delivered by needle (100) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (100) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

It should also be understood that the procedure described above may be carried out in accordance with any of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein.

III. Exemplary Injector System with Remote Control

In some versions of the procedure described above with reference to FIGS. 4A-4G and 5A-5C, the patient may be awake and under local anesthetic. In such instances, there is a risk of patient movement. Such patient movement while cannula (50) is disposed in the eye (301) may result in damage to the eye. In addition, operation of instrument (10) requires manual manipulation of actuation arms (24) and actuation knob (26). Such manually operable features may present a risk of unintended movement of cannula (50) within the eye (301). In addition, there may be difficulty in consistently achieving precise administration of bleb fluid (340) and therapeutic agent (341). It may therefore be desirable to mitigate risks associated with patient movement, to mitigate the risk of unintended movement of components that are disposed in the eye (301), and to enhance the consistency in the precision of administration of bleb fluid (340) and therapeutic agent (341).

Figure 6:
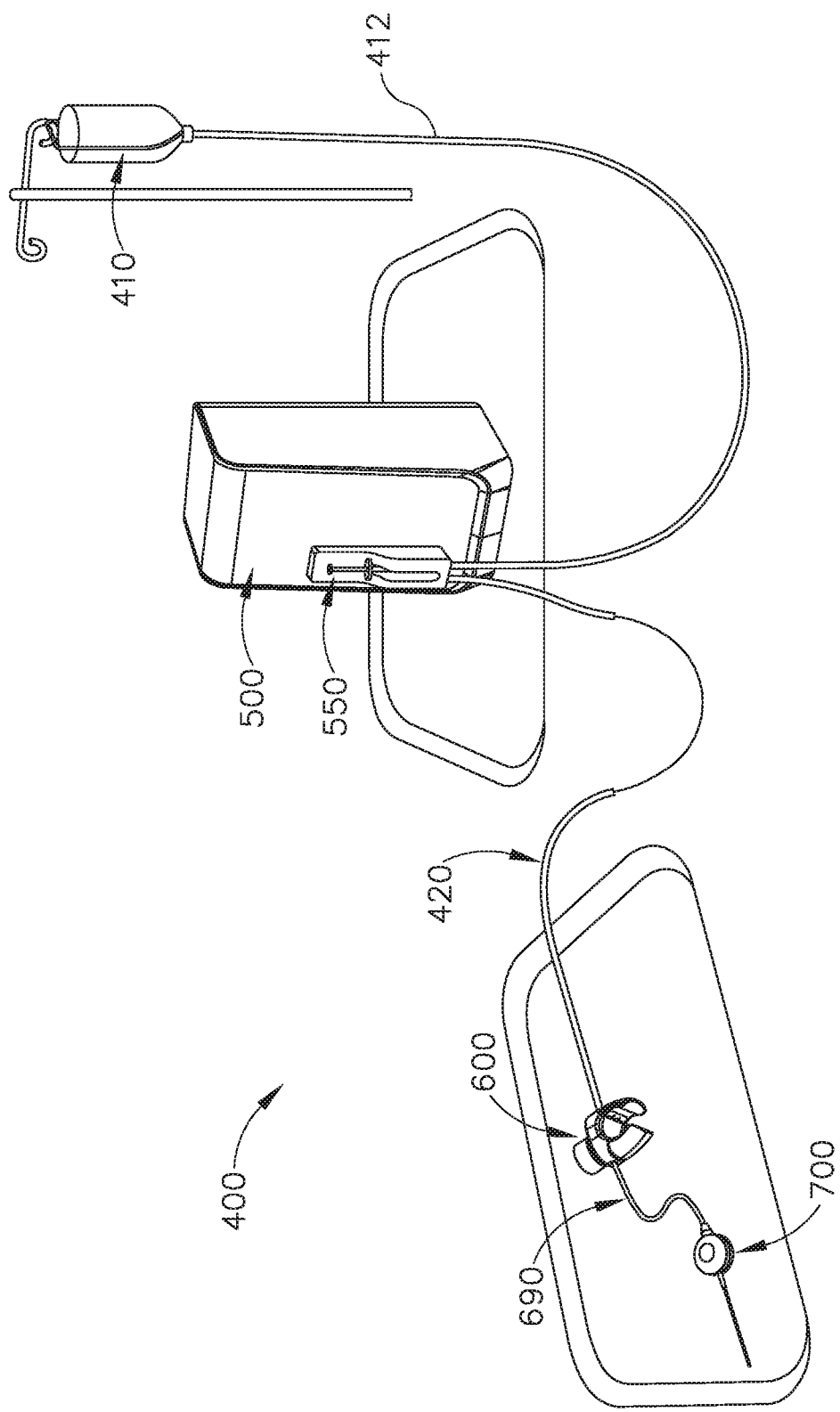
FIG. 6 depicts a perspective view of an exemplary system for subretinal administration of a therapeutic agent from a suprachoroidal approach.

FIG. 6 shows an exemplary system (400) that may be used to deliver bleb fluid (340) and therapeutic agent (341) into the eye (301) of a patient. System (400) of this example includes a control module (500), an injector driver assembly (600), and an injector assembly (700). A syringe actuation cassette (550) is disposed in control module (500) and is coupled with injector driver assembly (600) via a tube set (420). Syringe actuation cassette (550) is also coupled with a balanced salt solution (BSS) bottle (410) via a conduit (412). Injector assembly (700) is coupled with injector driver assembly (600) via a tube and cable assembly (690). Each of these components will be described in greater detail below.

Figure 7:
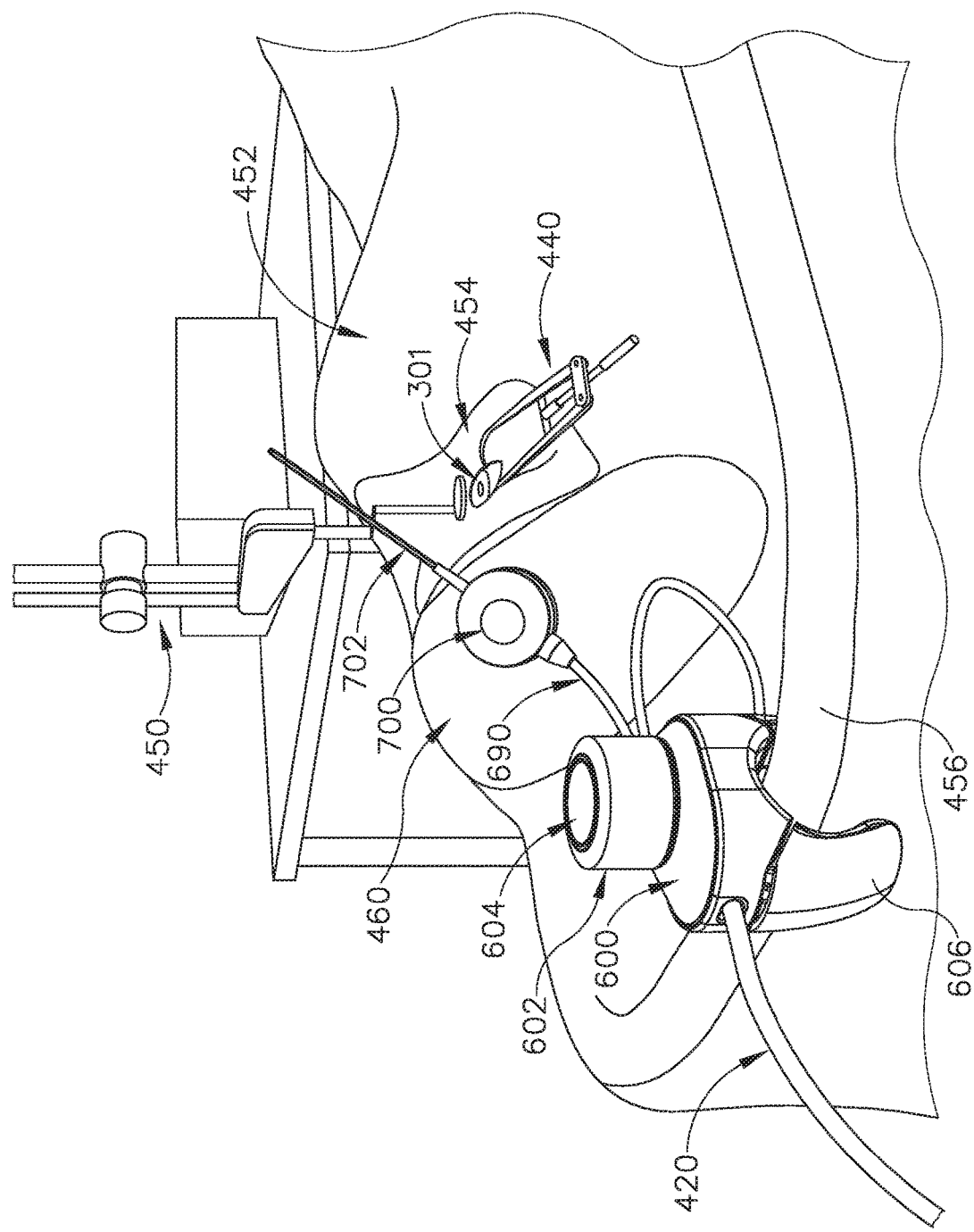
FIG. 7 depicts a perspective view of components of the system of FIG. 6 mounted near a patient.

FIG. 7 shows components of system (400) positioned in relation to a patient. In this example, a drape (452) is disposed over the patient, with an opening (454) formed in drape (452) near the patient's eye (301). A speculum (440) is used to keep the eye (301) open. A fixture (450) is positioned adjacent to the eye (301). Fixture (450) may be used to secure instrumentation, such as a viewing scope, relative to the patient. Magnetic pad (460) is adhered to drape (452) near the opening (454) adjacent to the eye (301). Injector assembly (700) is placed on magnetic pad (460), and is removably secured thereto via magnetic attraction as will be described in greater detail below. Injector assembly (700) is oriented to enable insertion of a flexible cannula (702) of injector assembly (700) into the eye (301). Injector driver assembly (600) is removably secured to a wrist rest (456) via arms (606). Injector driver assembly (600) is positioned close enough to injector assembly (700) to provide some degree of slack in tube and cable assembly (690). While not shown in FIG. 7, injector driver assembly (600) is coupled with control module (500) via syringe actuation cassette (550) and tube set (420).

Control module (500) of the present example is constructed and operable in accordance with the teachings of U.S. patent application Ser. No. 15/609,457, entitled "Injection Device for Subretinal Delivery of Therapeutic Agent," filed on filed on May 31, 2017, the disclosure of which is incorporated by reference herein. Syringe actuation cassette (550) is also constructed and operable in accordance with the teachings of U.S. patent application Ser. No. 15/609,457. As described therein, control module (500) and syringe actuation cassette (550) are operable to automatically dispense bleb fluid (340) and therapeutic agent (341) to injector driver assembly (600) and injector assembly (700) via tube set (420). Magnetic pad (460) may also be constructed and operable in accordance with the teachings of U.S. patent application Ser. No. 15/609,457.

Figure 8:
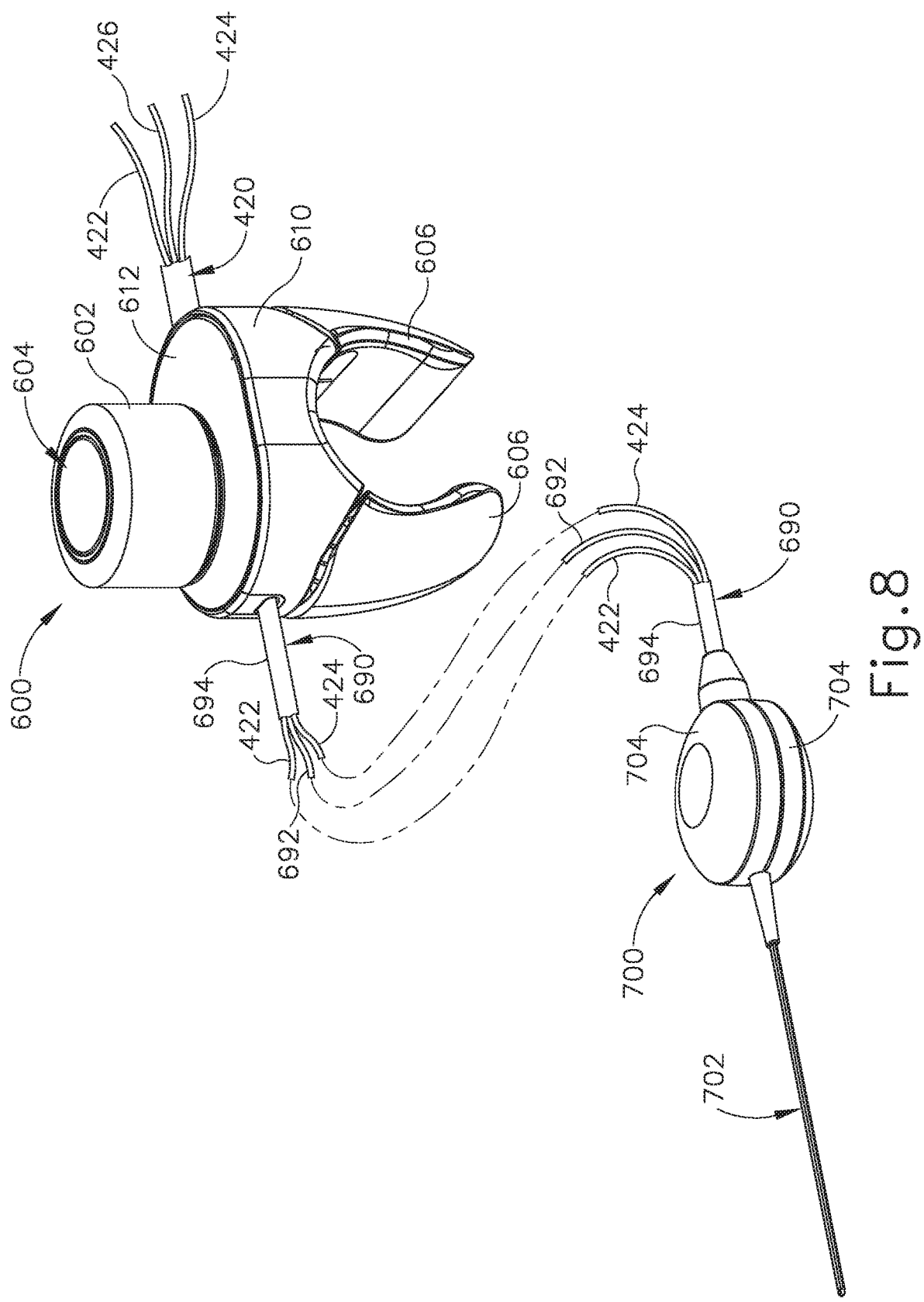
FIG. 8 depicts a perspective view of an exemplary injector assembly and an exemplary injector driver assembly of the system of FIG. 6.

FIG. 8 shows injector driver assembly (600) coupled with injector assembly (700) via tube and cable assembly (690). As shown in FIG. 8, conduits (422, 424) and electrical cable enter the proximal end of injector driver assembly (600) as part of tube set (420). Conduit (422) is configured to communicate bleb fluid (430) from BSS bottle (410); while conduit (424) is configured to communicate therapeutic agent from a syringe contained in syringe actuation cassette (550). Conduits (422, 424) pass through injector driver assembly (600), exiting the distal end of injector driver assembly (600) as part of tube and cable assembly (690). Conduits (422, 424) enter the proximal end of injector assembly (700) as part of tube and cable assembly (690). Tube and cable assembly (690) also includes a push-pull cable (692), which is operable to transfer longitudinal movement from injector driver assembly (600) to injector assembly (700) as will be described in greater detail below. Tube and cable assembly (690) also includes an outer sheath (694). Outer sheath (694) is configured to contain conduits (422, 424) and push-pull cable (692). Outer sheath (694) is also configured to serve as a longitudinal mechanical ground with respect to push-pull cable (692), such that push-pull cable (692) translates relative to outer sheath (694).

As shown in FIG. 8, injector assembly (700) of the present example comprises a pair of housing halves (704) with a cannula (702) extending distally therefrom. Cannula (702) may be constructed and operable like cannula (50) described above. A needle (not shown) is slidably disposed in cannula (702). This needle may be constructed and operable like needle (100) described above. The proximal end of the needle is secured to an actuator (not shown), which is slidably disposed in housing halves (704). The actuator is also secured to push-pull cable (692). Thus, when injector driver assembly (600) dives push-pull cable (692) longitudinally, the needle of injector assembly (700) will correspondingly translate relative to cannula (702). By way of example only, injector assembly (700) may be constructed and operable in accordance with the teachings of U.S. patent application Ser. No. 15/609,457.

FIGS. 9-17B show injector driver assembly (600) and components thereof in greater detail. While conduits (422, 424) are omitted from FIGS. 9-17B, it should be understood that conduits (422, 424) pass through injector driver assembly (600) as noted above. As shown, injector driver assembly (600) of the present example comprises a knob (602), a pushbutton (604), a body (610), and an upper rocker plate (612). A pair of arms (606) are pivotably coupled to body (610) and are operable to secure injector driver assembly (600) to a wrist rest (456) as noted above. Injector driver assembly (600) may include one or more resilient member (e.g., torsion springs, leaf springs, etc.) to resiliently bias arms (606) toward each other, to thereby urge arms (606) to grasp wrist rest (456).

Figure 9:
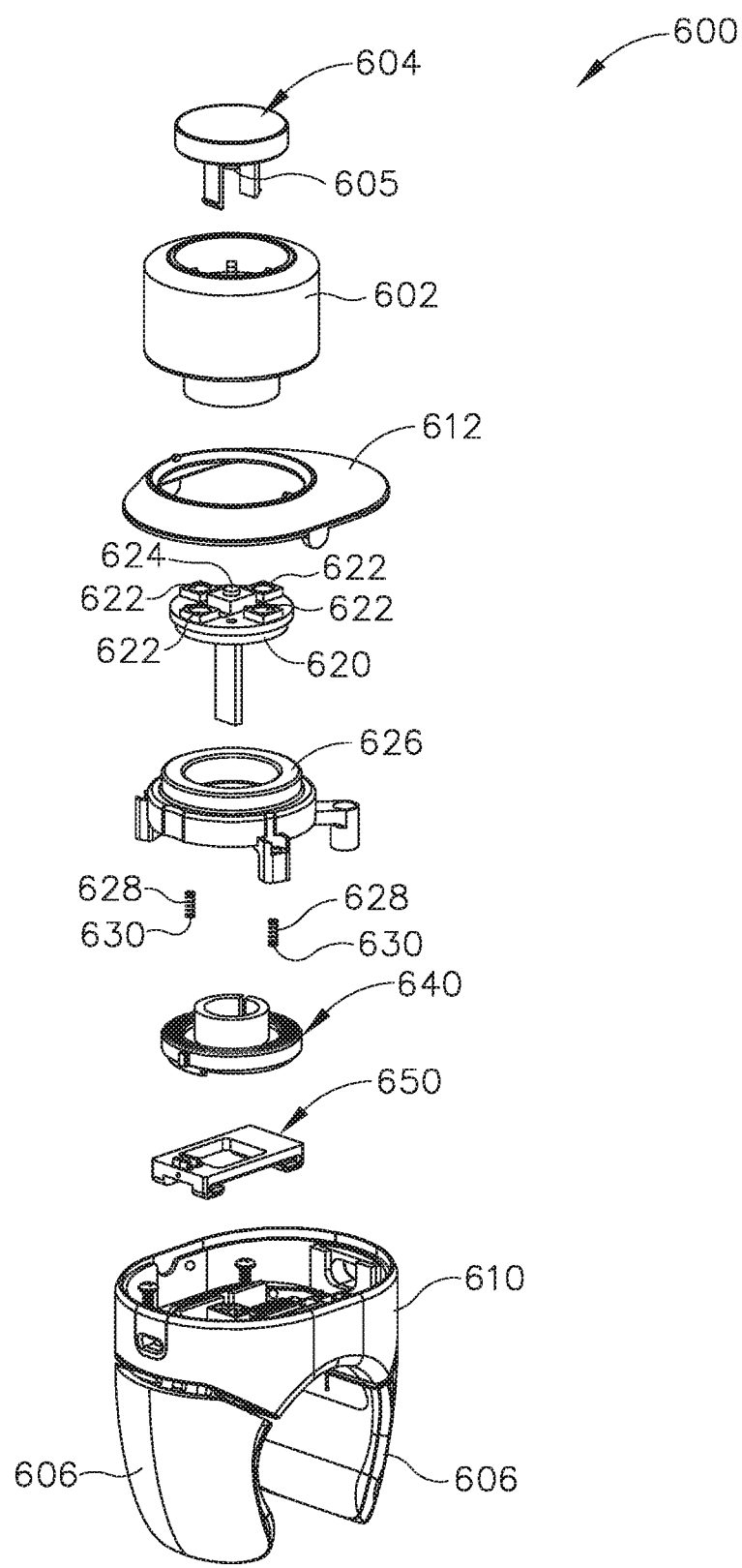
FIG. 9 depicts an exploded perspective view of the injector driver assembly of FIG. 8.

Knob (402), rocker pushbutton (604), plate (612), and body (610) are configured to cooperate to house several internal components within injector driver assembly (600). As shown in FIG. 9, these internal components include an array of RGB programmable LEDs (622) and a first tactile switch (624), all of which are mounted to a disc-shaped platform (620). The internal components further include an annular frame (626), a rotary cam member (640), a cam follower (650), a set of coil springs (628), and a set of ball bearings (630). Knob (402), pushbutton (604), and cam member (640) are coupled together such that knob (402), pushbutton (604), and cam member (640) are rotatable relative to the other components of injector driver assembly (600).

Pushbutton (604) is configured to reciprocate vertically within knob (402). A stud (605) (FIG. 9) projects downwardly from the underside of stud (605) and is configured to actuate tactile switch (624) when pushbutton (604) is pressed downwardly relative to knob (402). Tactile switch (624) is in communication with control module (500) via electric cable (426). In the present example, control module (500) is configured to initiate dispensation of therapeutic agent (341) through conduit (422) in response to tactile switch (624) being actuated via pushbutton (604). In some other versions, control module (500) is configured to initiate dispensation of bleb fluid (340) through conduit (424) in response to tactile switch (624) being actuated via pushbutton (604).

LEDs (622) are configured to selectively illuminate. Knob (402) and pushbutton (604) are configured to enable viewing of light emitted by LEDs (622). LEDs (622) may illuminate differently based on the particular state of system (400). For instance, LEDs (622) may illuminate in red when system (400) is not ready for actuation of pushbutton (604); and in green when system (400) is ready for actuation of pushbutton (604). As another merely illustrative example, LEDs (622) may illuminate in green when the needle of injector assembly (700) is in a fully proximal, retracted position; in yellow when the needle of injector assembly (700) is in an intermediate position but not yet extending from cannula (702); and in violet when the needle of injector assembly (700) is in a distally advanced position where the needle of injector assembly (700) protrudes from cannula (702). Other suitable ways in which LEDs (622) may be used will be apparent to those of ordinary skill in the art in view of the teachings herein.

Figure 10:
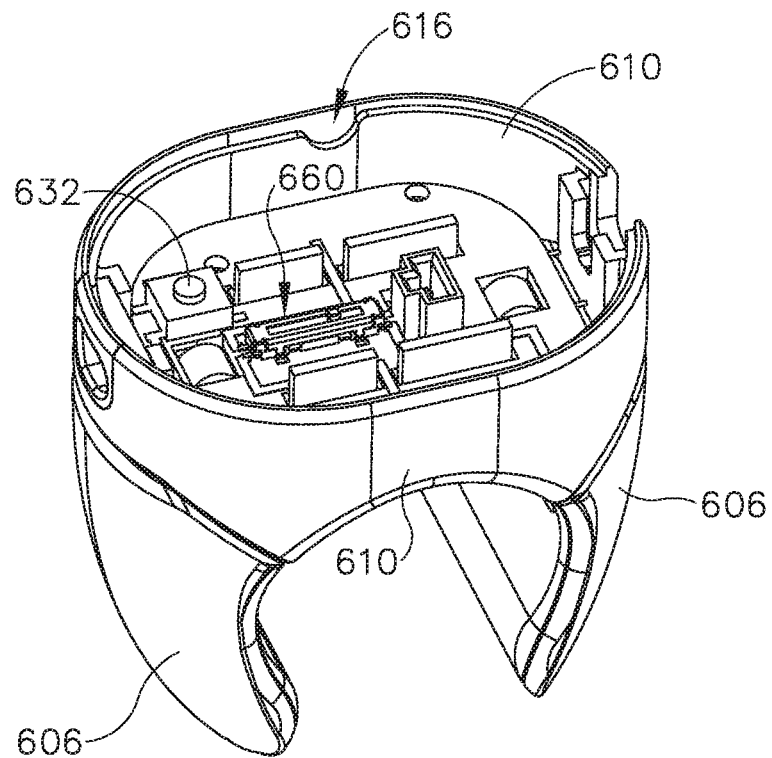
FIG. 10 depicts a perspective view of a bottom portion of the injector driver assembly of FIG. 8.

As shown in FIG. 10, another tactile switch (632) is located within body (610). Tactile switch (632) is configured to be actuated by upper rocker plate (612), as will be described in greater detail below. A linear sensor (660) is also located within body (610). Linear sensor (660) is configured to be actuated by cam follower (650), as will be described in greater detail below. Tactile switch (632) and linear sensor (660) are both in communication with control module (500) via electric cable (426).

Figure 11:
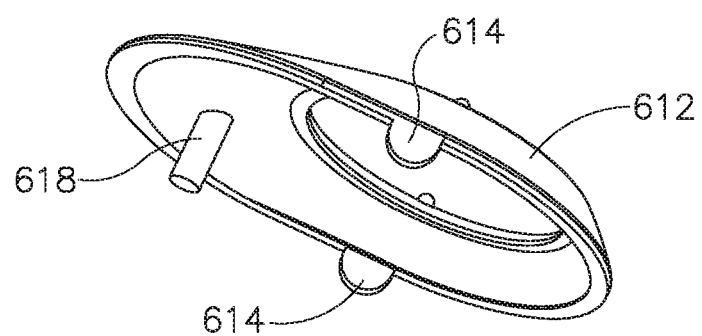
FIG. 11 depicts a perspective view of an upper rocker plate of the injector driver assembly of FIG. 8.

FIG. 11 shows rocker plate (612) in greater detail. As shown, rocker plate (612) includes a pair of downwardly projecting tabs (614) and a downwardly projecting stud (618). Tabs (614) are rounded and are configured to fit in complementary recesses (616) (FIG. 10) of body (610). This configuration of tabs (614) and recesses (616) allows rocker plate (612) to be rocked in such a way to enable stud (618)

to selectively actuate tactile switch (632). In the present example, control module (500) is configured to initiate dispensation of bleb fluid (340) through conduit (422) in response to tactile switch (632) being actuated via rocker plate (612). In some other versions, control module (500) is configured to initiate dispensation of therapeutic agent (341) through conduit (424) in response to tactile switch (632) being actuated via rocker plate (612).

Figure 12:
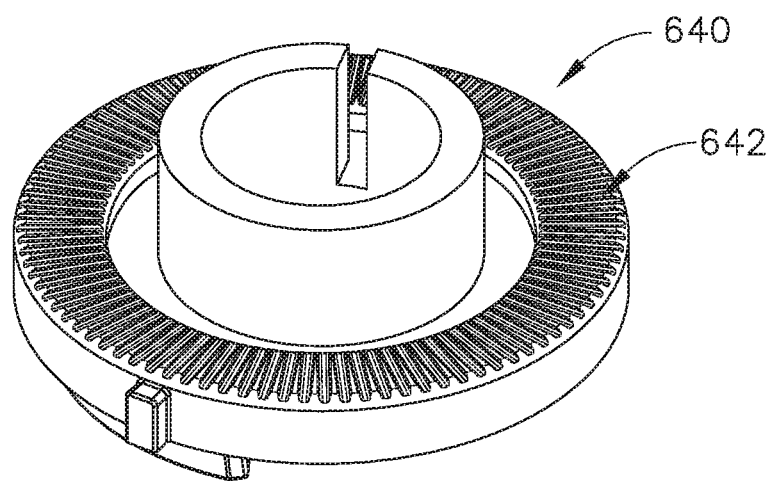
FIG. 12 depicts a perspective view of a rotary cam member of the injector driver assembly of FIG. 8.
Figure 13:
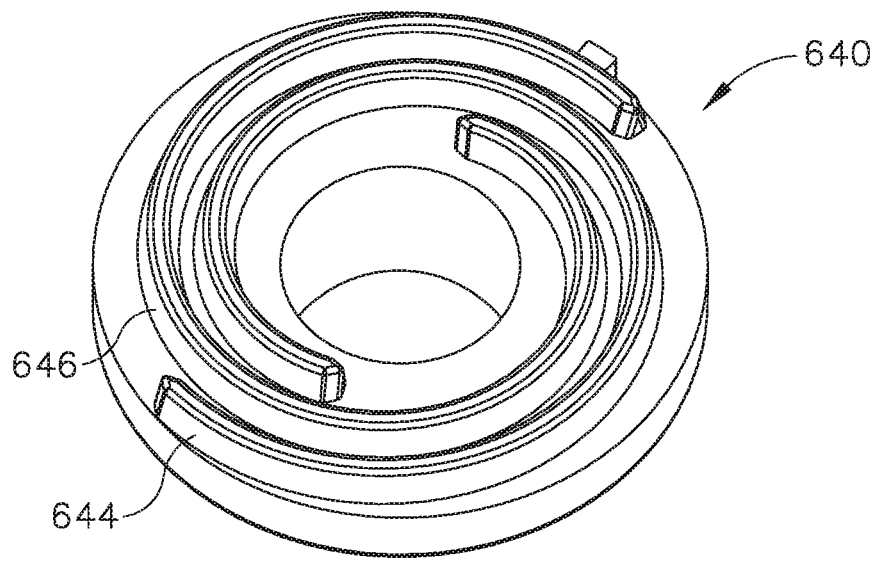
FIG. 13 depicts another perspective view of the rotary cam member of FIG. 12.

FIGS. 12-13 show rotary cam (640) in greater detail. As shown in FIG. 12, the upper side of rotary cam (640) includes an annular array of teeth (642) arranged in a starburst pattern. Teeth (642) are configured to engage ball bearings (630). An upper end of each coil spring (628) bears against the underside of annular frame (626), which serves as a mechanical ground. The lower end of each spring contacts a respective ball bearing (630) and thereby resiliently urges ball bearings (630) into engagement with teeth (642). The relationship between ball bearings (630) and teeth (642) provides enough resistance to rotation of knob (602) and rotary cam (640) to prevent inadvertent rotation of knob (602) and rotary cam (640); yet still permits intentional rotation of knob (602) and rotary cam (640). The resistance provided by ball bearings (630) and teeth (642) may also enable the operator to achieve a greater degree of precision in rotating knob (602) than the operator might otherwise achieve in the absence of such resistance. Other suitable kinds of structures that may be used instead of coil springs (628), ball bearings (630), and teeth (642) will be apparent to those of ordinary skill in the art in view of the teachings herein.

As shown in FIG. 13, the underside of rotary cam (640) includes a first spiral cam feature (644) and a second spiral cam feature (646). While spiral cam features (644, 646) are generally positioned about the radial center of rotary cam (640), spiral cam features (644, 646) are offset from the radial center of rotary cam (640) and from each other.

Figure 14:
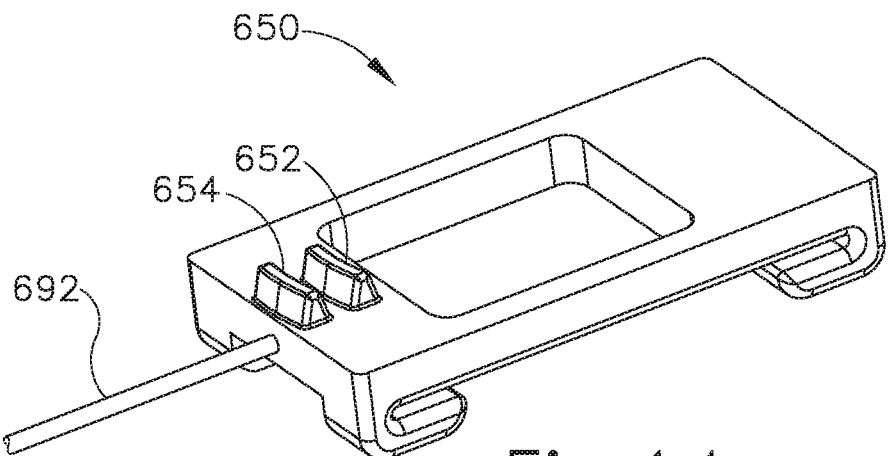
FIG. 14 depicts a perspective view of a cam follower of the injector driver assembly of FIG. 8.
Figure 15:
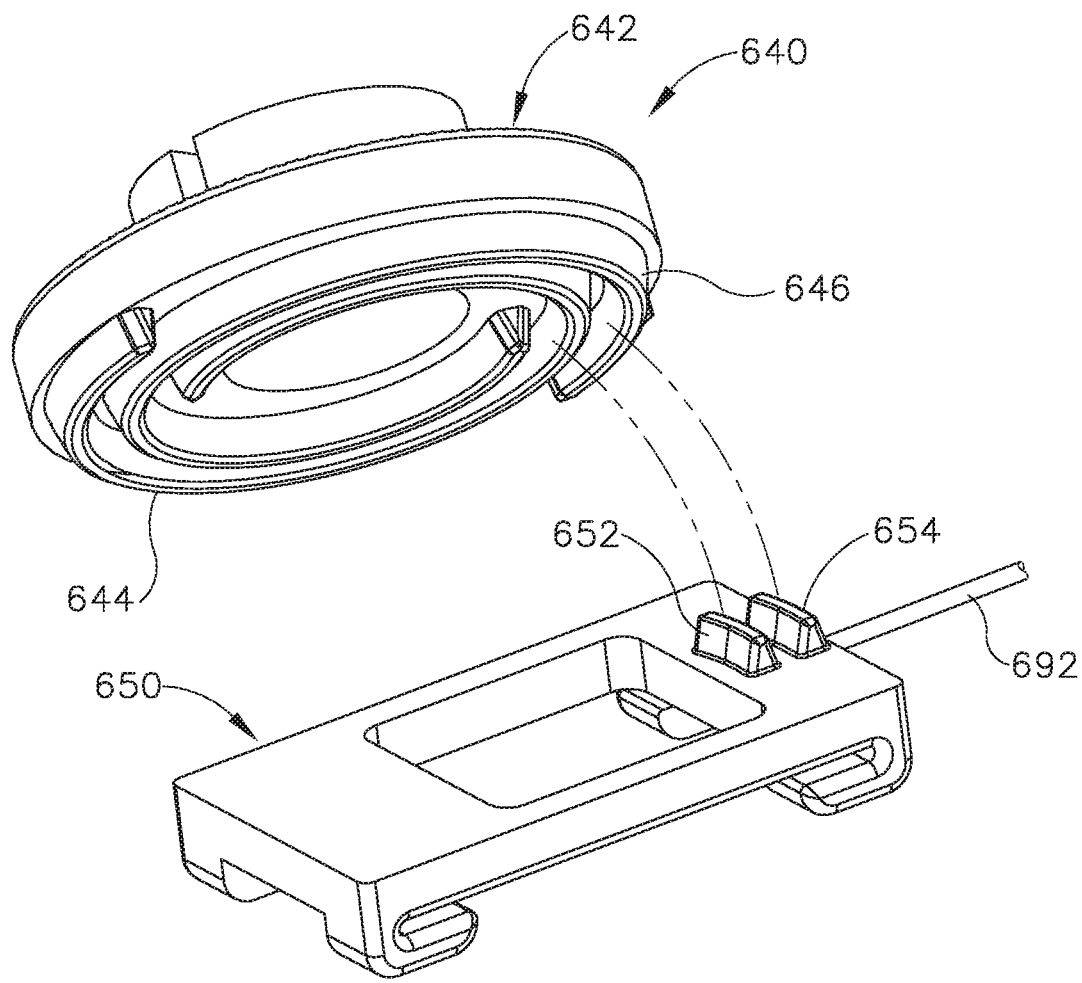
FIG. 15 depicts an exploded perspective view of the rotary cam member of FIG. 12 and the cam follower of FIG. 14.

As shown in FIG. 14, cam follower (650) of the present example includes a first upwardly projecting cam fin (652) and a second upwardly projecting cam fin (654). The proximal end of push-pull cable (692) is fixedly secured to cam follower (650). Cam fins (652, 654) are each contoured to complement the contours of spiral cam features (644, 646). As shown in FIG. 15, cam fin (652) is configured to fit in a first space between spiral cam features (644, 646); and cam fin (654) is configured to fit in a second space between spiral cam features (644, 646).

Figure 16A:
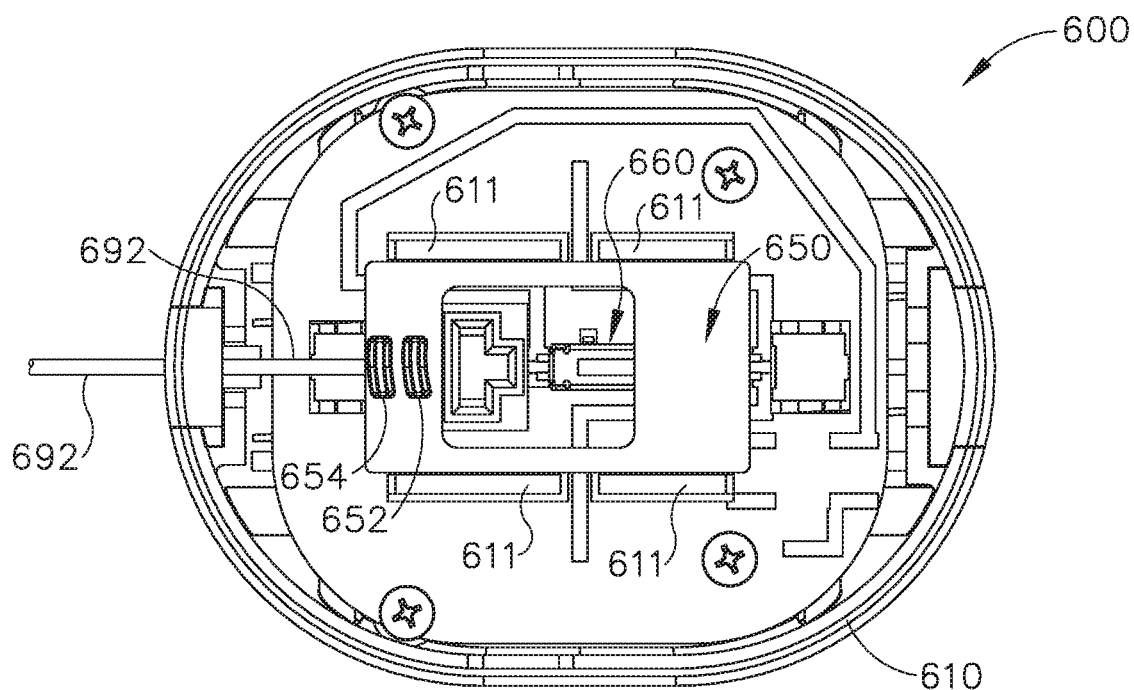
FIG. 16A depicts a top plan view of the injector driver assembly of FIG. 8, with an upper portion removed, and with the cam follower of FIG. 14 in a proximal position.
Figure 16B:
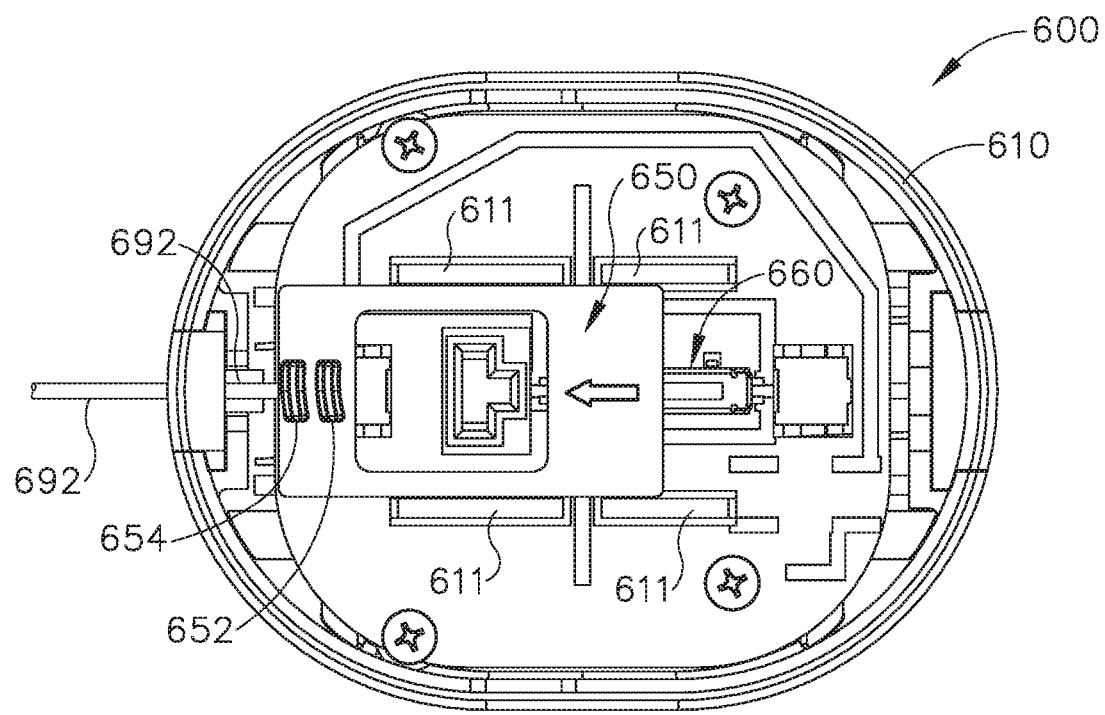
FIG. 16B depicts a top plan view of the injector driver assembly of FIG. 8, with an upper portion removed, and with the cam follower of FIG. 14 in a distal position.
Figure 17A:
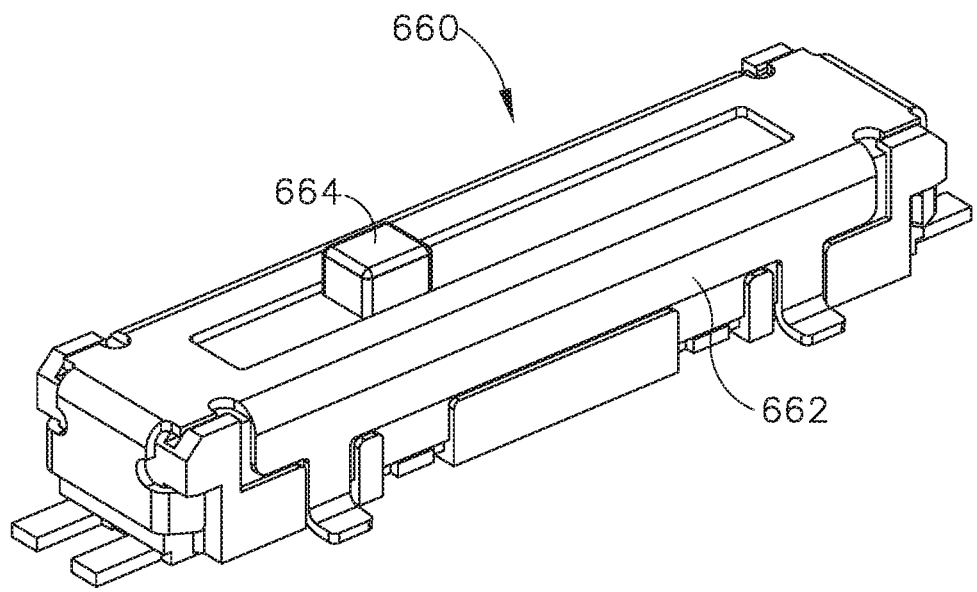
FIG. 17A depicts a perspective view of an exemplary linear sensor of the injector driver assembly of FIG. 8, with a slider of the sensor in a proximal position.
Figure 17B:
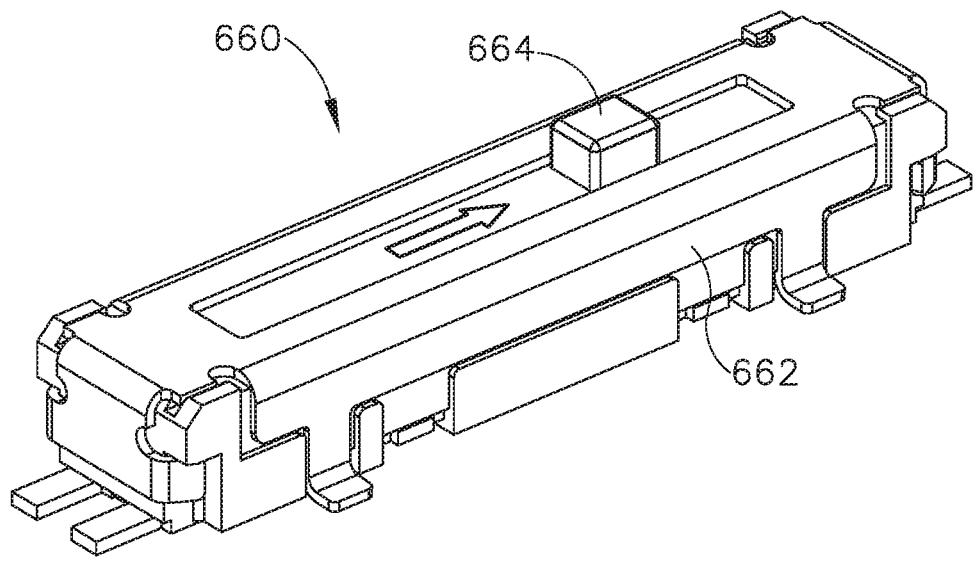
FIG. 17B depicts a perspective view of the linear sensor of FIG. 17A, with the slider of the sensor in a distal position.

Due to the engagement between cam fins (652, 654) and spiral cam features (644, 646), rotation of rotary cam (640) will cause cam follower (650) to translate longitudinally along the longitudinal axis of push-pull cable (692). Such translation is shown in FIGS. 16A-16B. As shown in FIGS. 16A-16B, cam follower (650) is captured between a set of bosses (611), which are unitary features of body (610). Bosses (611) are configured to guide and laterally support cam follower (650) as cam follower (650) translates between a proximal position (FIG. 16A) and a distal position (FIG. 16B). As noted above, push-pull cable (692) is fixedly secured to cam follower (650). Push-pull cable (692) is also fixedly secured to needle actuator (not shown), which is further fixedly secured to the needle of injector assembly (700). It should therefore be understood that the needle of injector assembly (700) will translate distally and proximally relative to cannula (702) in response to rotation of knob (602) relative to body (610).

Rotary cam (640) and cam follower (650) are mere examples of features that may be used to drive push-pull cable (692) longitudinally. By way of example only, an alternative drive assembly may include a pull-pull cable with a reversing pulley wheel (e.g., inside injector assembly (700)). By way of further example only, an alternative drive assembly may include an electrical line in tube and cable assembly (690); and a micromotor inside injector assembly (700). By way of further example only, an alternative drive assembly may include an electrical line in tube and cable assembly (690); and a nano-muscle nitinol wire inside injector assembly (700). By way of further example only, an alternative drive assembly may include a fluid drive line in tube and cable assembly (690); and a piston-cylinder assembly in injector assembly (700) to provide a hydraulic drive assembly, with spring return.

The underside of cam follower (650) is secured to a slider (664) of linear sensor (660). Slider (664) is configured to translate longitudinally relative to a body (662) of linear sensor (660). Since cam follower (650) is secured to slider (664), slider (664) will be in a proximal position (FIG. 17A) when cam follower (650) is in a proximal position (FIG. 16A); and slider (664) will be in a distal position (FIG. 17B) when cam follower (650) is in a distal position (FIG. 16B). Linear sensor (660) is configured to generate a varying data value based on the longitudinal position of slider (664) along body (662). By way of example only, linear sensor (660) may comprise a linear potentiometer that generates a varying resistance value based on the longitudinal position of slider (664) along body (662). Thus, the resistance value generated through linear sensor (660) will be indicative of the longitudinal position of the needle of injector assembly (700) relative to cannula (702). By way of further example only, linear sensor (660) may comprise a sensor that senses rotation of knob (602), an optical sensor, or a sensor located in injector assembly (700) to directly monitor movement of needle actuator (not shown). Various other suitable ways in which movement of the needle of injector assembly (700) may be sensed will be apparent to those of ordinary skill in the art in view of the teachings herein.

Since linear sensor (660) is in communication with control module (500), control module (500) may control the delivery of bleb fluid (340) and/or therapeutic agent (341) via conduits (422, 424) based on the longitudinal position of the needle of injector assembly (700) relative to cannula (702) as sensed by linear sensor (660). In the present example, whenever linear sensor (660) detects distal advancement of the needle of injector assembly (700), the corresponding signal sent to control module (500) will automatically trigger delivery of bleb fluid (340). This ensures that bleb fluid (340) will flow out through the distal tip of the needle of injector assembly (700) any time the needle of injector assembly (700) is advanced, on a consistent basis. By ensuring such bleb fluid (340) flow on a consistent basis, system (400) may minimize the risk of accentual perforation of the retina (308).

In some versions, control module (500) is programmed such that bleb fluid (340) is automatically delivered at a predetermined rate, based on advancement of the needle of injector assembly (700) as sensed by linear sensor (660). Even in instances where bleb fluid (340) delivery is automated, control module (500) may still be responsive to actuation of tactile switch (632) to deliver additional bleb fluid (340) at a predetermined rate, independent of the longitudinal position of the needle of injector assembly (700). It should also be understood that the delivery of therapeutic agent (341) may also be provided by control module (500) at a predetermined rate, to deliver a predetermined volume, in response to actuation of tactile switch (624). Moreover, the delivery of therapeutic agent (341) may be fully automated as soon as the operator actuates tactile switch (624) via pushbutton (604). In other words, the operator may not be able to selectively stop (and perhaps re-start) the delivery of therapeutic agent (341) once the operator has actuated tactile switch (624). Thus, the duration at which pushbutton (604) is depressed, or the repeated press and release of pushbutton, etc., may have no effect on the delivery of therapeutic agent (341) once the operator has actuated tactile switch (624). Other examples of ways in which delivery of bleb fluid (340) and/or therapeutic agent (341) may be automatically provided based on the sensed position of the needle of injector assembly (700) are described in greater detail below.

In an exemplary use, the operator may arrange magnetic pad (460), injector driver assembly (600), and injector assembly (700) as shown in FIG. 7. The operator may then form a sclerotomy in the eye (301) of the patient and insert cannula (702) into the eye (301) via the sclerotomy. To assist in the formation of the sclerotomy, the operator may use a marking instrument as described in U.S. patent application Ser. No. 15,609/419, filed on May 31, 2017, the disclosure of which is incorporated by reference herein. To assist in the insertion of cannula (702) into the sclerotomy along a substantially tangential path, the operator may use a guide track as described in U.S. patent application Ser. No. 15,609/419, the disclosure of which is incorporated by reference herein. As another merely illustrative alternative, the operator may use a suture loop assembly (332). Cannula (702) may then be advanced to position as shown in FIGS. 4C-4D with reference to cannula (50).

With cannula (702) positioned as shown in FIGS. 4C-4D with reference to cannula (50), the operator may then rotate knob (602) to advance the needle of injector assembly (700) distally as shown in FIGS. 4E and 5A with reference to needle (100). During this advancement of the needle of injector assembly (700), control module (500) will automatically provide bleb fluid (340) through the needle of injector assembly (700) based on a signal from linear sensor (660), ultimately resulting in a configuration similar to that shown in FIGS. 4G and 5B. After the needle of injector assembly (700) has been sufficiently advanced, the operator actuates pushbutton (604). This causes control module (500) to provide therapeutic agent (341) through the needle of injector assembly (700), ultimately resulting in a configuration similar to that shown in FIGS. 4H and 5C. The operator then rotates knob (602) in reverse to retract the needle of injector assembly (700) back into cannula (702). With the needle of injector assembly (700) retracted, the operator then withdraws cannula (702) from the eye (301) and securely closes the sclerotomy using any suitable technique.

IV. Exemplary Injector Assembly with Integrated Control

While the combination of injector driver assembly (600), injector assembly (700), and push-pull cable (692) may enable greater safety, precision, and consistency in the delivery of therapeutic agent (341) to the eye (301), it may be desirable to provide the same results using instrumentation that is more compact. Reducing the instrument form factor and eliminating push-pull cable (692) may provide instrumentation that is easier to handle; and may remove some hysteresis that might otherwise occur and potentially have an adverse effect on the precision of control. To that end, FIGS. 18-19 show an exemplary alternative injector assembly (800) that is operable to provide the same results that are provided by injector driver assembly (600), injector assembly (700), and push-pull cable (692), but through a more compact device.

Figure 18:
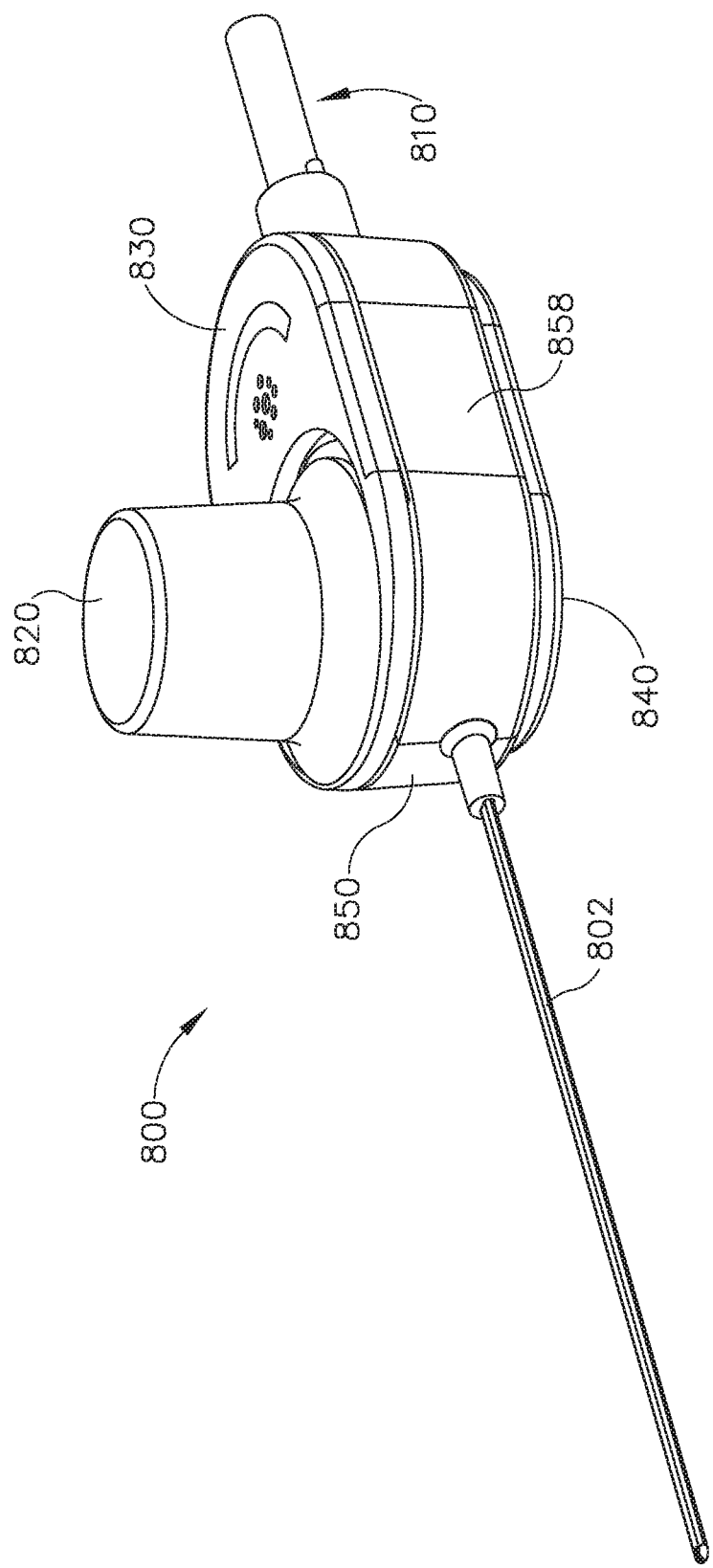
FIG. 18 depicts a perspective view of an exemplary alternatively injector assembly that may be incorporated into the system of FIG. 6.
Figure 19:
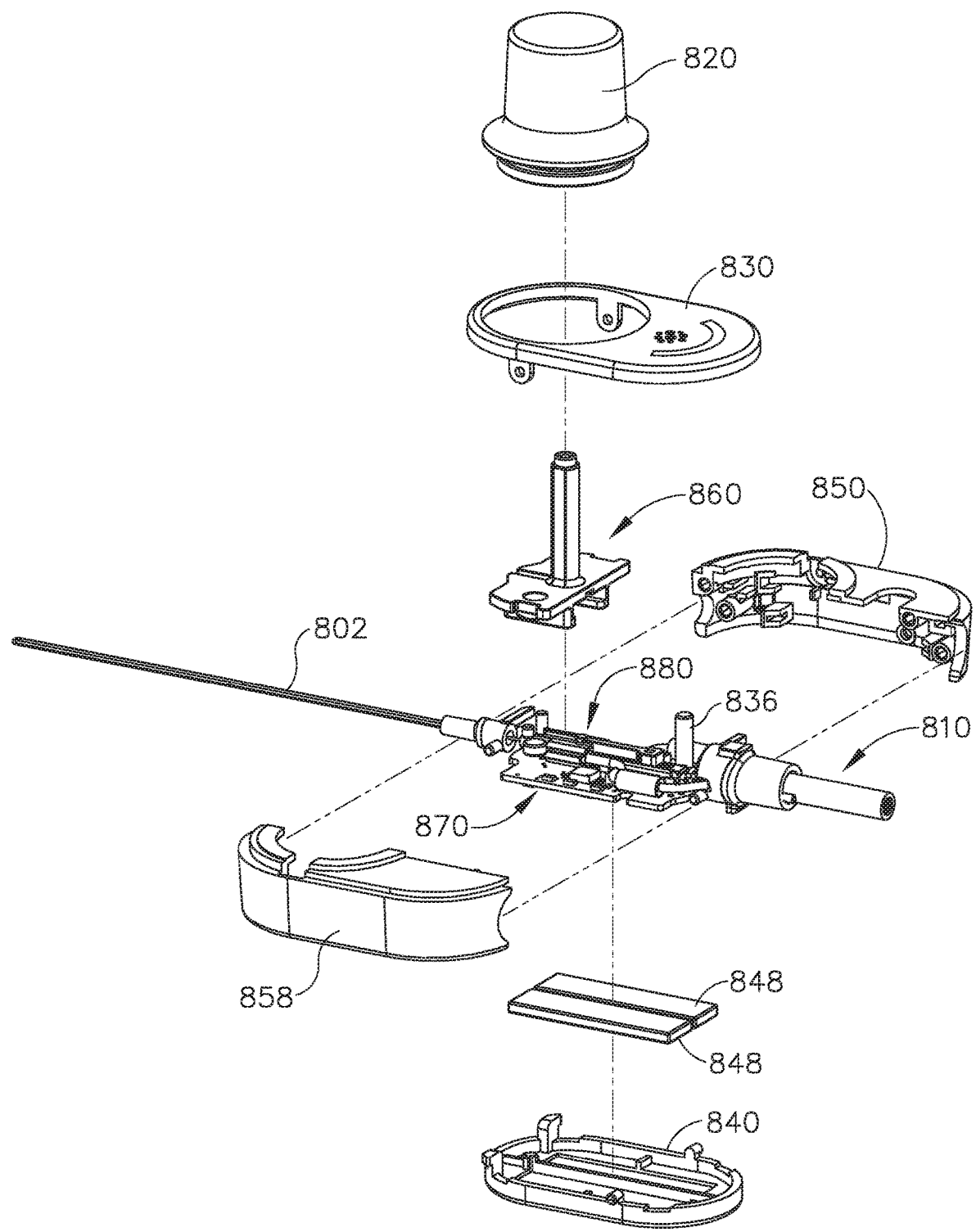
FIG. 19 depicts an exploded perspective view of the injector assembly of FIG. 18.

As shown in FIG. 18, injector assembly (800) of this example comprises a cannula (802), a rotary knob (820), an upper rocker plate (830), a lower rocker plate (840), and a pair of housing halves (850, 858). As shown in FIG. 19, injector assembly (800) further includes a frame member (860), a circuit board assembly (870), a needle driver/needle actuator (880), and a pair of magnets (848). A tube set (810) extends proximally from injector assembly (800). Each of these components and associated components will be described in greater detail below.

Figure 20A:
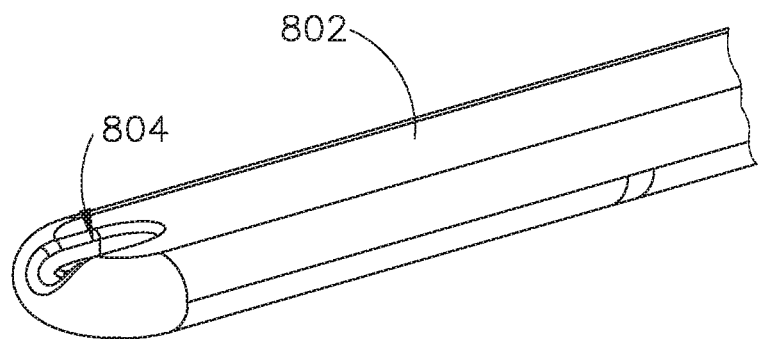
FIG. 20A depicts a perspective view of the distal end of a cannula of the injector assembly of FIG. 18, with a needle retracted in the cannula.
Figure 20B:
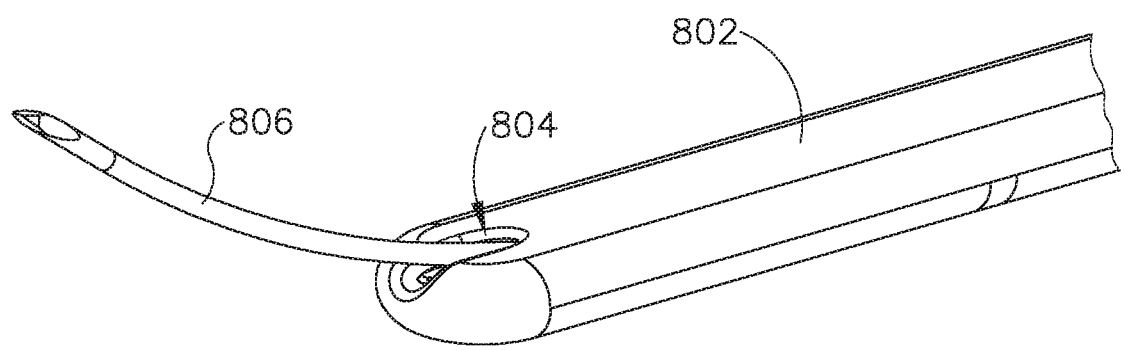
FIG. 20B depicts a perspective view of the distal end of a cannula of FIG. 20A, with a needle extending from the cannula.

As shown in FIGS. 20A-20B, cannula (802) of this example includes a distal, transversely oriented opening (804). A needle (806) is configured to be advanced distally through opening (804), as shown in FIG. 20B. In some versions, needle (806) has a preformed bend as described in U.S. patent application Ser. No. 15/438,918, entitled "Apparatus for Subretinal Administration of Therapeutic Agent via a Curved Needle," filed Feb. 22, 2017, the disclosure of which is incorporated by reference herein.

Figure 21:
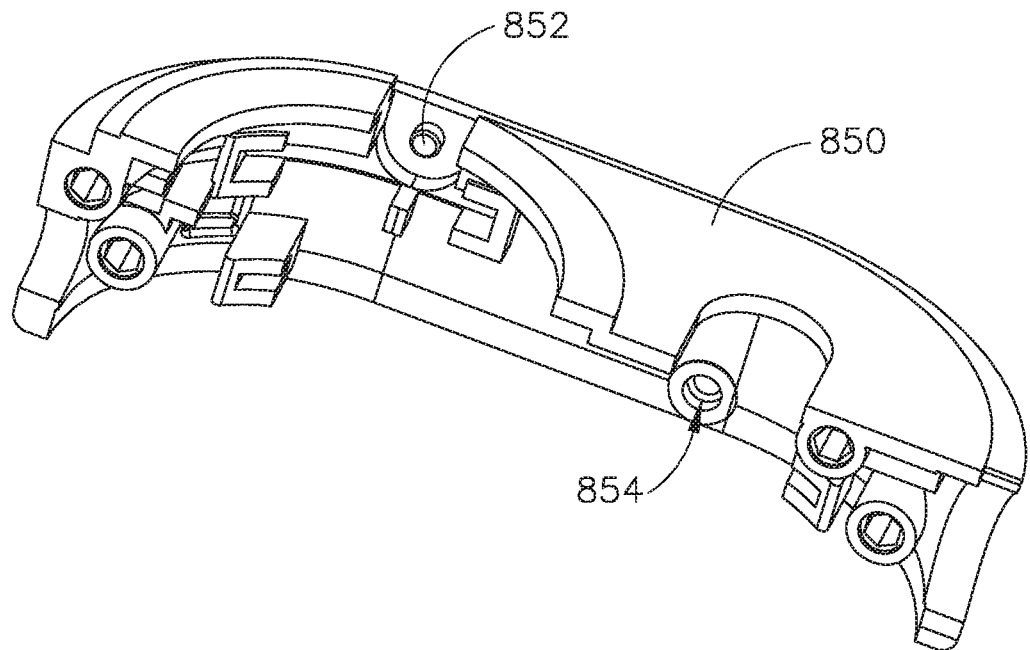
FIG. 21 depicts a perspective view of a housing half of the injector assembly of FIG. 18.
Figure 22:
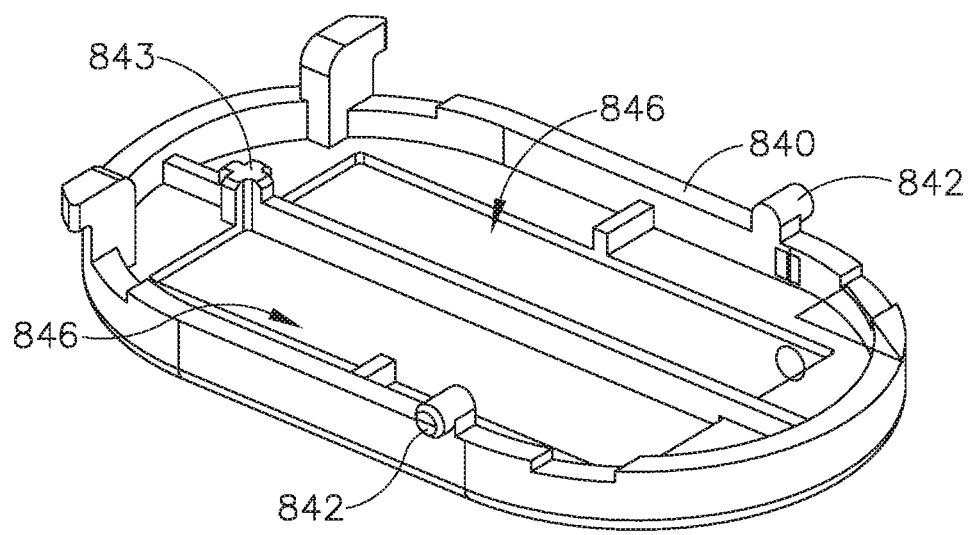
FIG. 22 depicts a perspective view of a lower rocker plate of the injector assembly of FIG. 18.
Figure 23:
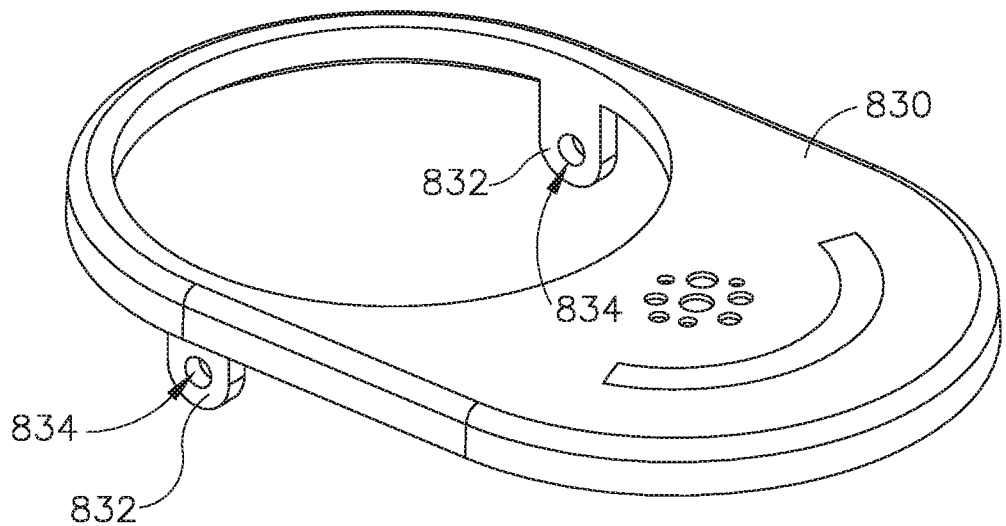
FIG. 23 depicts a perspective view of an upper rocker plate of the injector assembly of FIG. 18.
Figure 24:
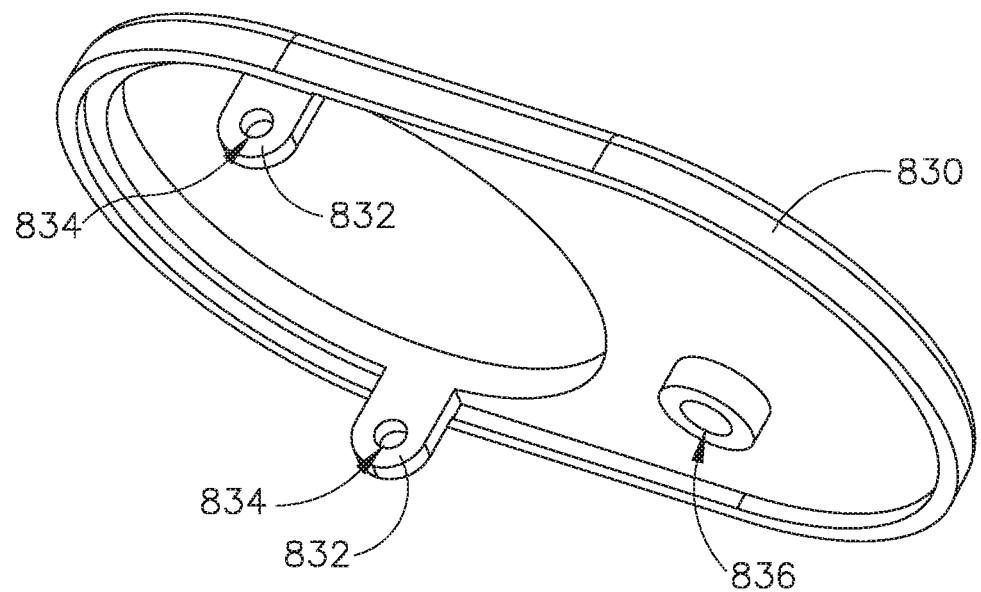
FIG. 24 depicts another perspective view of the upper rocker plate of FIG. 23.

As shown in FIG. 21, housing half (850) includes an inwardly extending integral pivot post (852) and an integral post seat (854). While not shown, it should be understood that housing half (858) may also include an inwardly extending integral pivot post (852) and an integral post seat (854). As shown in FIG. 22, lower rocker plate (840) includes a pair of outwardly extending pivot posts (842) that are positioned and configured to be seated in integral post seats (854) of housing halves (850, 858) to provide a pivotal coupling between lower rocker plate (840) and housing halves (850, 858). As shown in FIGS. 23-24, upper rocker plate (830) includes a pair of downwardly protruding tabs (832) with openings (834) formed therein. Openings (834) are positioned and configured to receive pivot posts (852) of housing halves (850, 858) to provide a pivotal coupling between lower rocker plate (840) and housing halves (850, 858).

Figure 25:
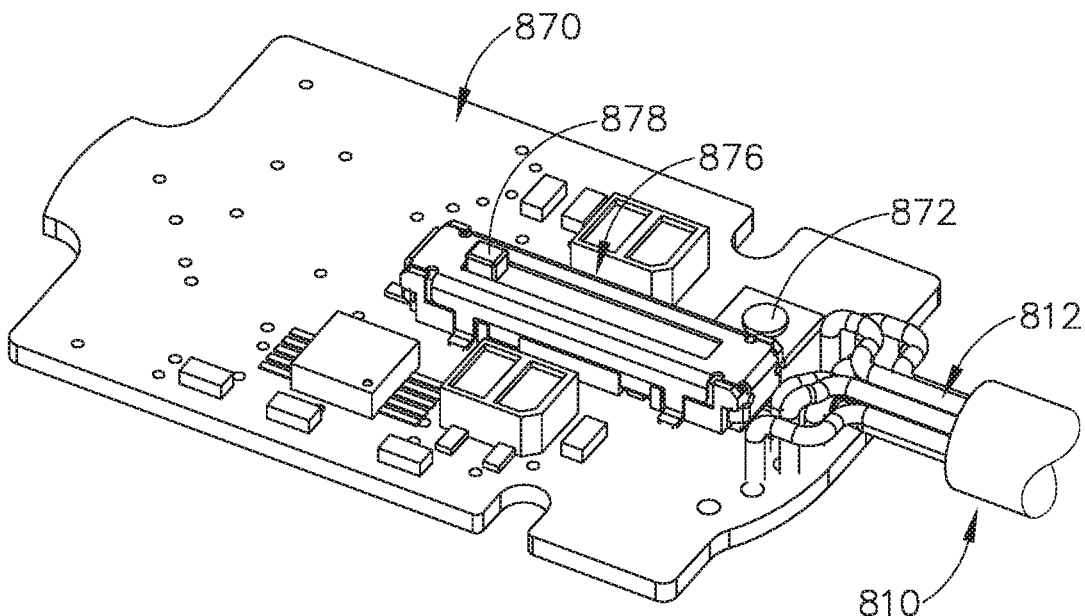
FIG. 25 depicts a perspective view of a circuit board assembly of the injector assembly of FIG. 18.

As shown in FIG. 25, an upper side of circuit board assembly (870) comprises a first tactile switch (872) and a linear sensor (876). First tactile switch (872) is positioned to be actuated by a dowel (836) (FIG. 19) that is positioned between first tactile switch (872) and a dowel seat (836) (FIG. 24) on the underside of upper rocker plate (840). The operator may provide such actuation of tactile switch (872) by pressing upper rocker plate (840) to cause upper rocker plate (840) to pivot about pivot posts (852), which will drive dowel (836) downwardly toward first tactile switch (872). First tactile switch (872) may communicate with control module (500) via one or more of wires (812) contained in tube set (810). By way of example only, control module (500) may provide delivery of therapeutic agent (341) via needle (806) in response to actuation of first tactile switch (872), similar to the delivery of therapeutic agent (341) via the needle of injector assembly (700) in response to actuation of tactile switch (624) as described above.

In the present example, tactile switch (872) is located near the proximal end of injector assembly (800); while tactile switch (874) is located near the distal end of injector assembly (800). In addition, the pivot points for upper rocker plate (830) are located near the distal end of injector assembly (800); while the pivot points for lower rocker plate (840) are located near the distal end of injector assembly (800). Positioning the pivot points and tactile switches (872, 874) in this way may reduce the risk of an operator inadvertently actuating tactile switch (872) while attempting to actuate tactile switch (874); and vice-versa.

Linear sensor (876) includes a slider (878) and is configured and operable just like linear sensor (660) described above. Linear sensor (876) is in communication with control module (500) via one or more of wires (812) contained in tube set (810). Control module (500) is configured to provide automated delivery of bleb fluid (340) via needle (806) in response to distal movement of needle (806) as sensed by linear sensor (876).

Figure 26:
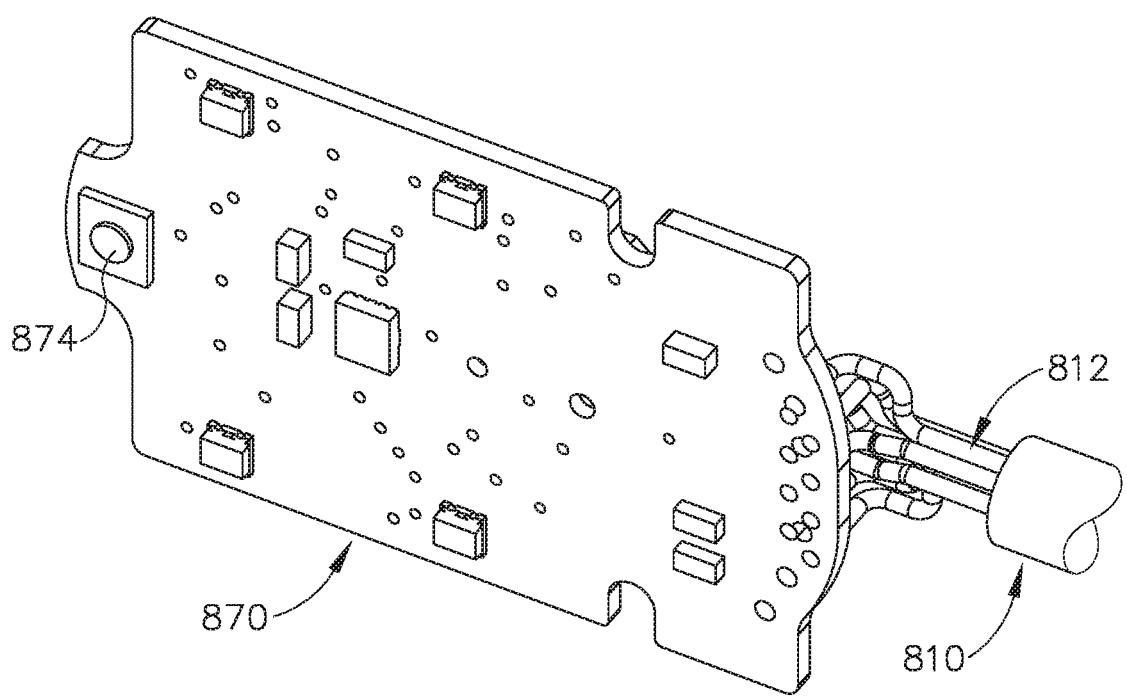
FIG. 26 depicts another perspective view of the circuit board assembly of FIG. 25.

As shown in FIG. 26, the underside of circuit board assembly (870) includes a second tactile switch (874). Second tactile switch (874) is positioned to be actuated by an integral post (843) (FIG. 22) of lower rocker plate (840). The operator may provide such actuation of tactile switch (874) by pivotably urging housing halves (850, 858) downwardly to cause housing halves (850, 858) to pivot about pivot posts (842), which will drive tactile switch (874) downwardly toward integral post (843). Second tactile switch (874) may communicate with control module (500) via one or more of wires (812) contained in tube set (810). By way of example only, control module (500) may provide delivery of bleb fluid (340) via needle (806) in response to actuation of second tactile switch (874), similar to the delivery of bleb fluid (340) via the needle of injector assembly (700) in response to actuation of tactile switch (632) as described above. Exemplary alternative methods of delivering bleb fluid (340) are described in greater detail below.

Referring back to FIG. 22, a pair of recesses (846) are formed in the bottom of lower rocker plate (840). Recesses (846) are configured to receive elongate magnets (848). Magnets (848) provide magnetic attraction to magnetic pad (460). Magnets (848) thus enable injector assembly (800) to be removably secured to magnetic pad (460), to be easily repositioned on magnetic pad (460), and to be easily removed from magnetic pad (460). As noted above, magnetic pad (460) may take a variety of alternative forms, and other suitable structures and techniques may be used to removably secure injector assembly (800) relative to a patient.

Figure 29:
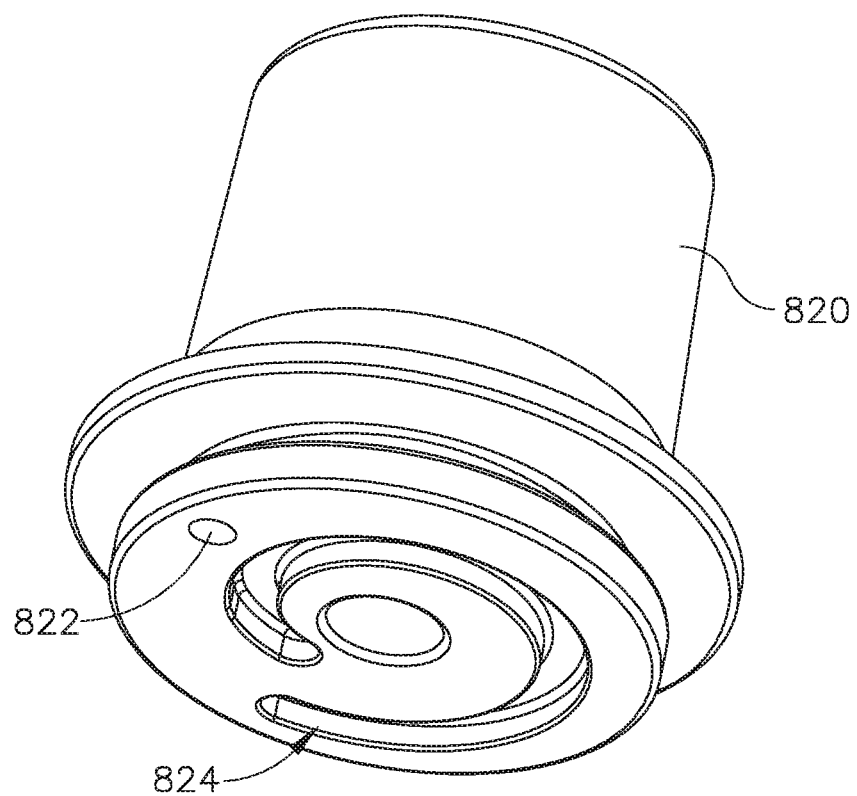
FIG. 29 depicts a perspective view of a rotary cam of the needle actuation assembly of FIG. 27.
Figure 30:
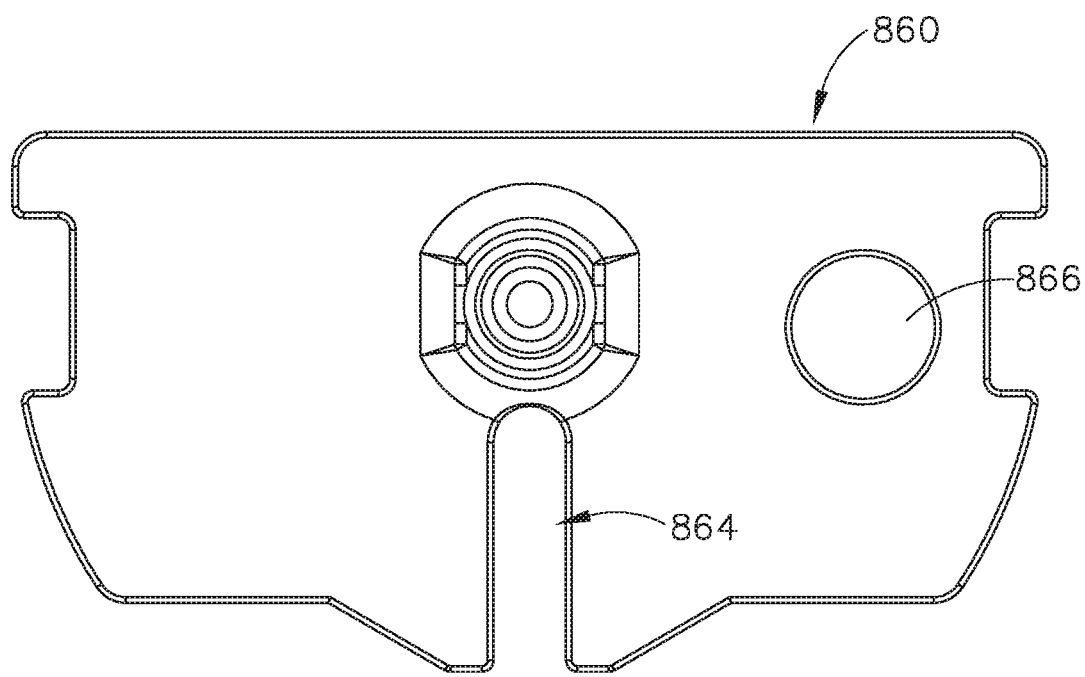
FIG. 30 depicts a top plan view of the frame member of FIG. 28.
Figure 31:
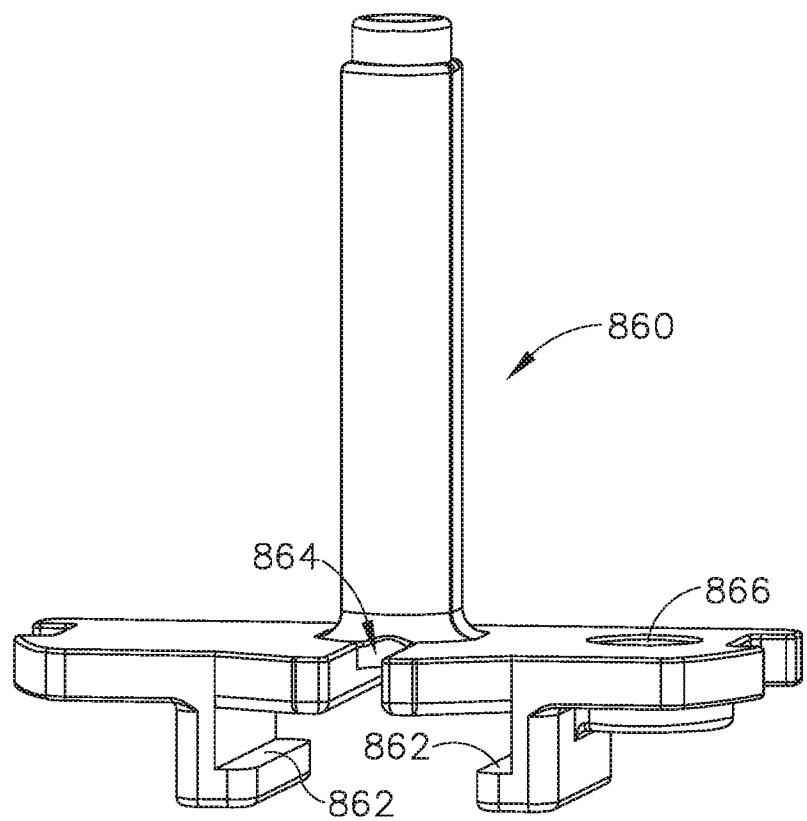
FIG. 31 depicts a perspective view of the frame member of FIG. 28.
Figure 32:
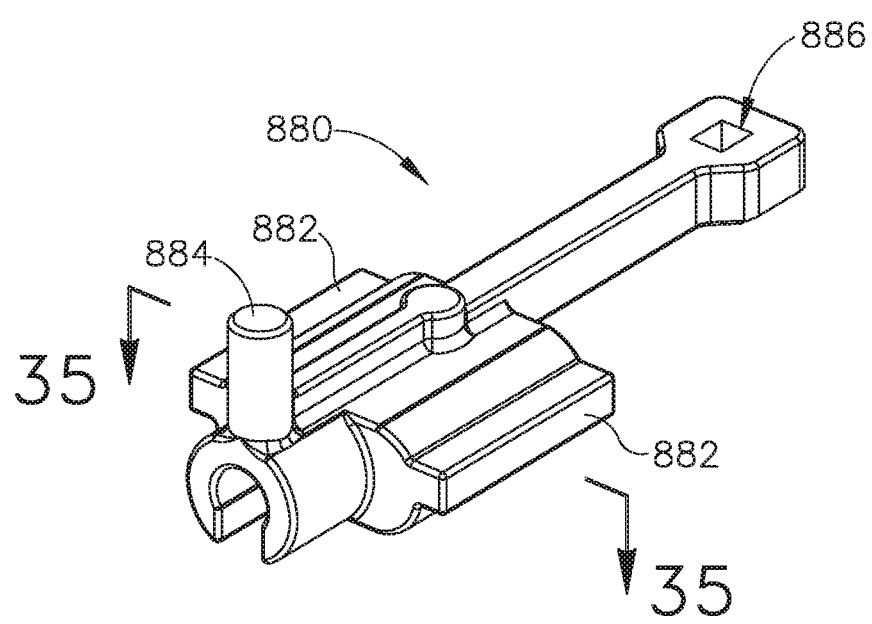
FIG. 32 depicts a perspective view of the needle driver of FIG. 28.

As shown in FIGS. 17-18, rotary knob (828), frame member (860), and needle actuator (880) are coupled together to form an assembly. Rotary knob (820) is operable to rotate relative to housing halves (850, 858). Frame member (860) is configured to be unitarily secured to housing halves (850, 858), such that frame member (860) remains stationary relative to housing halves (850, 858). Needle actuator (880) is operable to translate relative to housing halves (850, 858), in response to rotation of rotary knob (820) relative to housing halves (850, 858). As shown in FIG. 29, the underside of rotary knob (820) includes a spiral cam recess (824) and a magnet (822). As shown in FIGS. 30-31, frame member (860) includes a pair of support rails (862), a guide slot (864), and a magnet (866). As shown in FIG. 32, needle actuator (880) comprises a pair of guide wings (882), a cam follower post (884), and a proximal opening (886).

Figure 27:
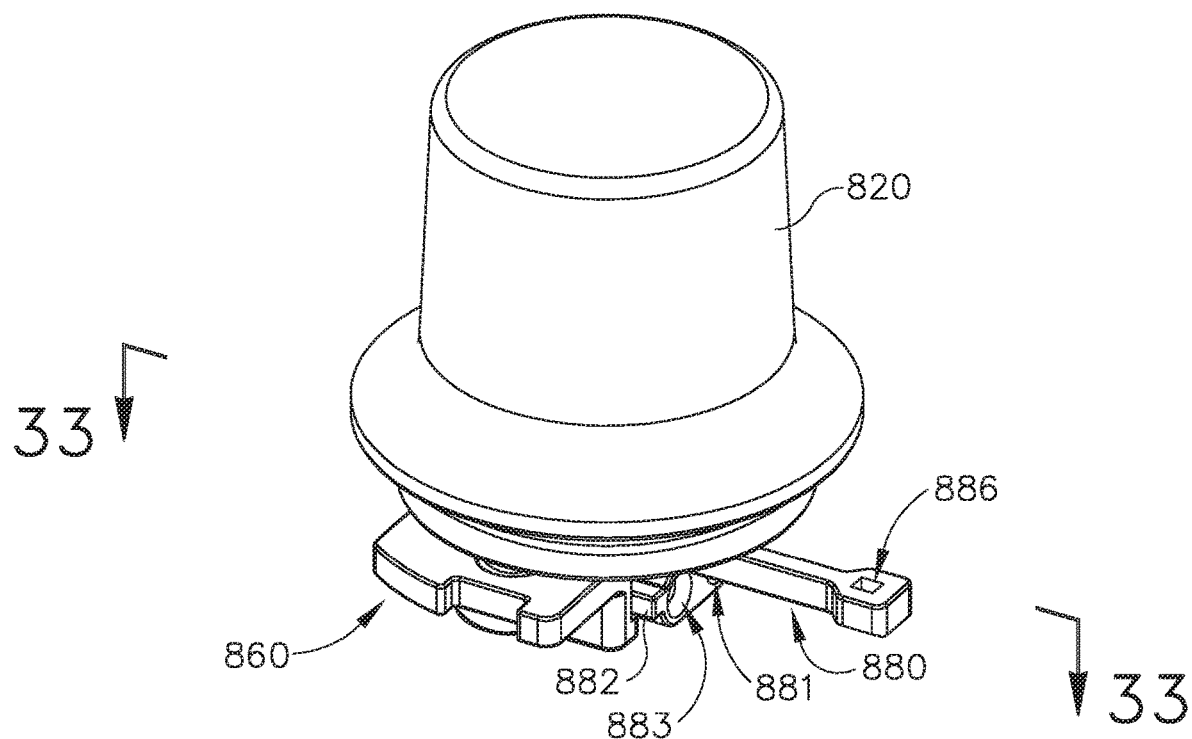
FIG. 27 depicts a perspective view of a needle actuation assembly of the injector assembly of FIG. 18.
Figure 28:
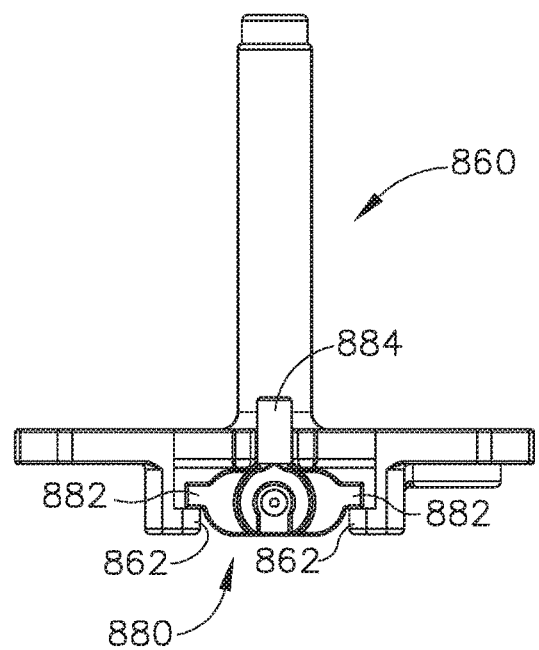
FIG. 28 depicts a front elevational view of a frame member and a needle driver of the needle actuation assembly of FIG. 27.

Referring back to FIGS. 27-28, guide wings (882) are sized and configured to engage support rails (862). This engagement provides vertical and lateral support to needle actuator (880), while permitting needle actuator (880) to slide longitudinally relative to frame member (860). Guide slot (864) is configured to receive cam follower post (884) and accommodate sliding movement thereof as needle actuator (880) slides longitudinally relative to frame member (860). Proximal opening (886) is positioned and configured to receive slider (878) of linear sensor (876), such that slider (878) will slide unitarily with needle actuator (880).

Figure 33A:
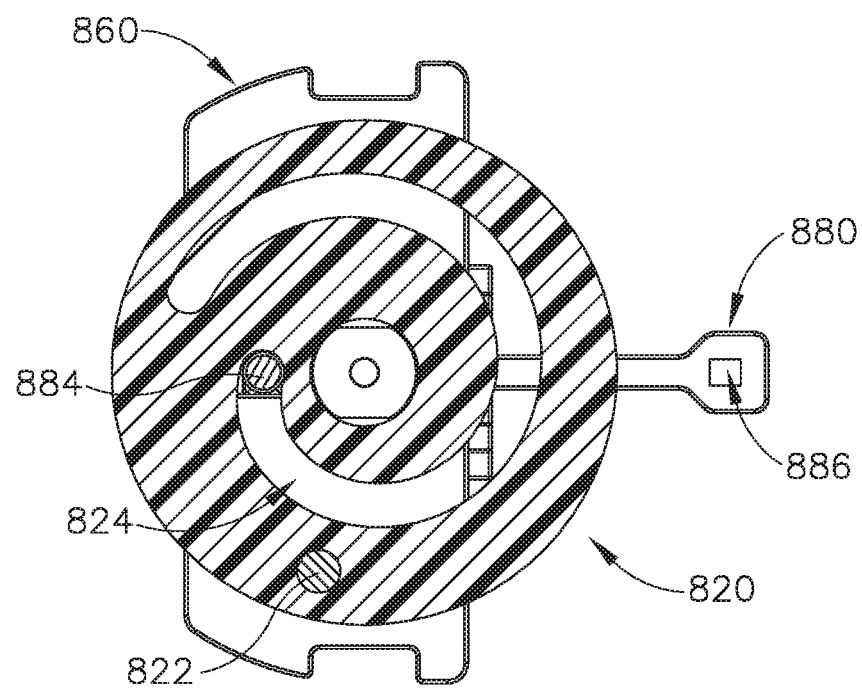
FIG. 33A depicts a cross-sectional view, taken along line 33-33 of FIG. 27, of the needle actuation assembly of FIG. 27, with the rotary cam of FIG. 29 at a first angular position and the needle driver of FIG. 28 in a proximal position.
Figure 33B:
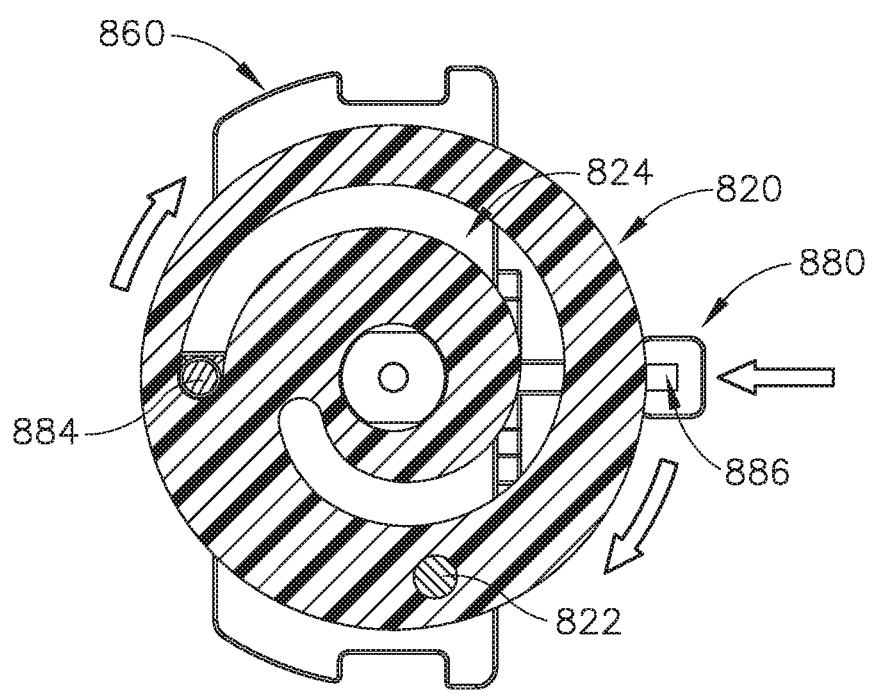
FIG. 33B depicts a cross-sectional view, taken along line 33-33 of FIG. 27, of the needle actuation assembly of FIG. 27, with the rotary cam of FIG. 29 at a second angular position and the needle driver of FIG. 28 in a distal position.

As shown in FIGS. 33A-33B, cam follower post (884) of needle actuator (880) is configured to fit in spiral cam recess (824) of rotary knob (820). Due to this engagement, and due to guidance provided to cam follower post (884) by guide slot (864), needle actuator (880) will translate from a proximal position (FIG. 33A) to a distal position (FIG. 33B) in response to rotation of rotary knob (820). Needle (806) is fixedly secured to needle actuator (880) as described in greater detail below, such that needle (806) will translate longitudinally relative to cannula (802) in response to rotation of rotary knob (820). In the present example, magnets (822, 866) are positioned such that magnet (822) will be located directly over magnet (866) when rotary knob (820) is in a home position as shown in FIG. 33A. In this stage, magnets (822, 866) prevent rotary knob (820) from being rotated inadvertently; yet permit intentional rotation of rotary knob (820). In some other variations, magnets (822, 866) are positioned such that magnet (822) will be located directly over magnet (866) when rotary knob (820) is in the fully rotated position as shown in FIG. 33B.

Figure 34:
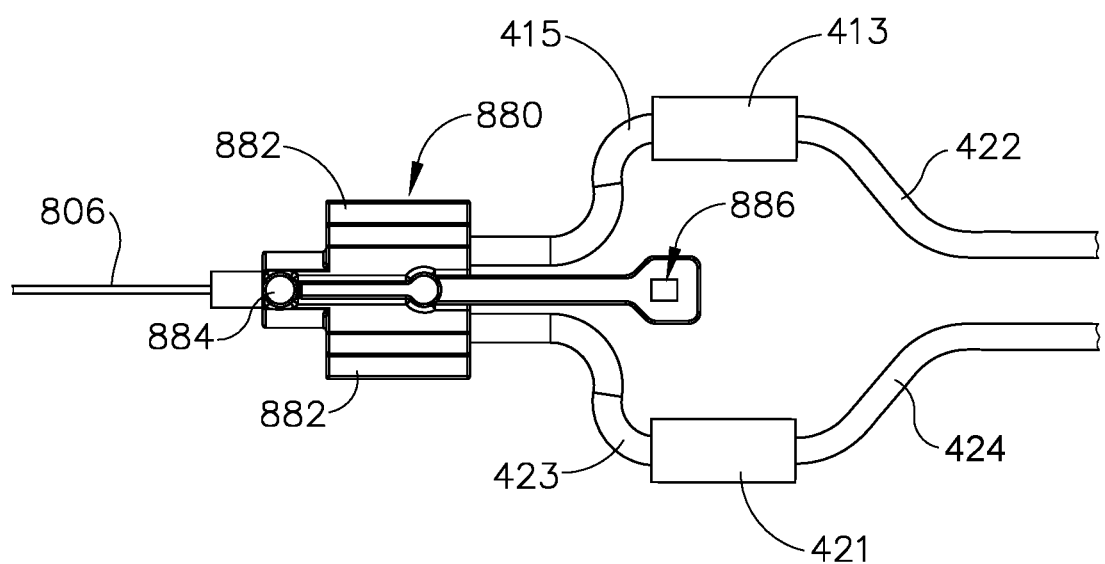
FIG. 34 depicts a top plan view of the needle driver of FIG. 28 with fluid conduits coupled thereto.
Figure 35:
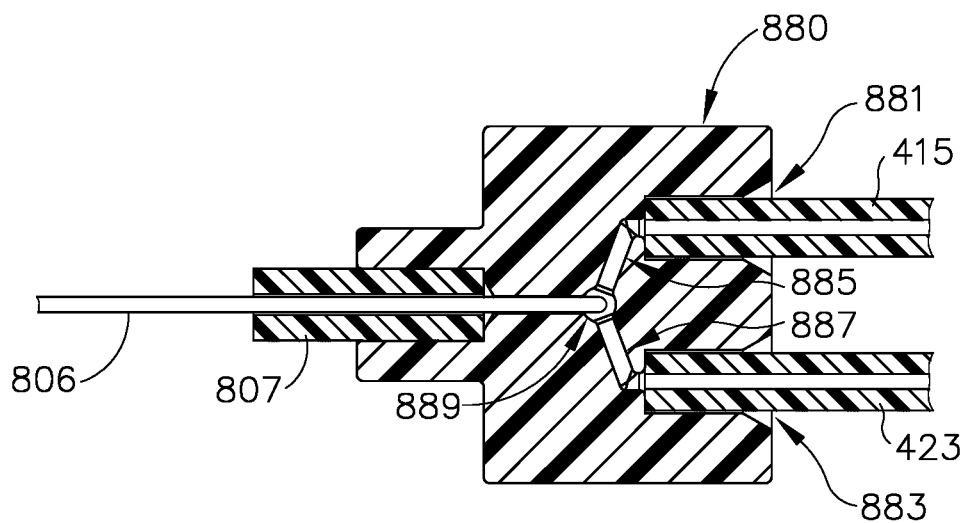
FIG. 35 depicts a cross-sectional view of the needle driver of FIG. 28, taken along line 35-35 of FIG. 32, with the fluid conduits of FIG. 34 coupled thereto.

As shown in FIGS. 34-35, needle (806) extends distally from the distal end of needle actuator (880) and is fixedly secured thereto by a ferrule (807). Conduits (415, 423) extend proximally from the proximal end of needle actuator (880). Conduit (415) is coupled with a one-way valve assembly (413), which is further coupled with conduit (422). As noted above, conduit (422) is in communication with syringe actuation cassette (550) and is configured to deliver bleb fluid (340) from BSS bottle (410). One-way valve assembly (413) is configured to provide fluid delivery only from conduit (422) to conduit (415); and to prevent fluid delivery from conduit (415) to conduit (422). Conduit (423) is coupled with a one-way valve assembly (421), which is further coupled with conduit (424). As noted above, conduit (424) is in communication with syringe actuation cassette (550) and is configured to deliver therapeutic agent (431). One-way valve assembly (421) is configured to provide fluid delivery only from conduit (424) to conduit (423); and to prevent fluid delivery from conduit (423) to conduit (424). Various structures that may be incorporated into one-way valve assemblies (413, 421) will be apparent to those of ordinary skill in the art in view of the teachings herein. Conduits (422, 424) are integrated into tube set (810), along with wires (872).

As shown in FIG. 35, the distal end of conduit (415) is inserted into a proximal opening (881) of needle actuator (880), while the distal end of conduit (423) is inserted into another proximal opening (883) of needle actuator (880). Proximal opening (881) is in fluid communication with a lumen (885) formed in needle actuator (880), while proximal opening (883) is in fluid communication with a lumen (887) formed in needle actuator (880). Lumens (885, 887) are in fluid communication with a chamber (889) formed in needle actuator (880). The proximal end of needle (806) is positioned in chamber (889). Thus, needle (806) receives fluids (840, 841) communicated through conduits (415, 413). Needle actuator (880) thus defines a fluid manifold.

In an exemplary use, the operator may arrange magnetic pad (460) as shown in FIG. 7, and place injector assembly (800) on magnetic pad (460). The operator may then form a sclerotomy in the eye (301) of the patient and insert cannula (802) into the eye (301) via the sclerotomy. To assist in the formation of the sclerotomy, the operator may use a marking instrument as described in U.S. patent application Ser. No.

15,609/419, the disclosure of which is incorporated by reference herein. To assist in the insertion of cannula (802) into the sclerotomy along a substantially tangential path, the operator may use a guide tack as described in U.S. patent application Ser. No. 15,609/419, the disclosure of which is incorporated by reference herein. As another merely illustrative alternative, the operator may use a suture loop assembly (332). Cannula (802) may then be advanced to position as shown in FIGS. 4C-4D with reference to cannula (50).

With cannula (802) positioned as shown in FIGS. 4C-4D with reference to cannula (50), the operator may then rotate knob (820) to advance needle (806) distally as shown in FIGS. 4E and 5A with reference to needle (100). During this advancement of needle (806), control module (500) will automatically provide bleb fluid (340) through needle (806) based on a signal from linear sensor (876), ultimately resulting in a configuration similar to that shown in FIGS. 4G and 5B. After needle (806) has been sufficiently advanced, the operator actuates upper rocker plate (830). This causes control module (500) to provide therapeutic agent (341) through needle (806), ultimately resulting in a configuration similar to that shown in FIGS. 4H and 5C. The operator then rotates knob (820) in reverse to retract needle (806) back into cannula (802). With needle (806) retracted, the operator then withdraws cannula (802) from the eye (301) and securely closes the sclerotomy using any suitable technique.

V. Exemplary Alternative Bleb Delivery Algorithms

As noted above, bleb fluid (340) may be dispensed through a needle (100, 806) as needle (100, 806) is being advanced distally, to prevent needle (100, 806) from piercing the retina (308). Bleb fluid (340) is dispensed automatically via control module (500), which may allow various programming options to coordinate the automated delivery of bleb fluid (340). Automated delivery of bleb fluid (340) may eliminate risks that may otherwise be present in versions where bleb fluid (340) is delivered manually (e.g., via a foot pedal, etc.). For instance, if bleb fluid (340) is delivered too early (e.g., before needle (100, 806) penetrates the choroid (306), the bleb fluid (340) may undesirably enter the suprachoroidal space. When bleb fluid (340) enters the suprachoroidal space, bleb fluid (340) may raise the choroid (306) and the retina (308), which may make it more difficult to achieve the proper angle of entry for needle (100, 806) to properly penetrate the choroid (306). If bleb fluid (340) is delivered too early or too late (e.g., after needle (100, 806) passes through the choroid (306) and enters the subretinal space), then the safety function of bleb fluid (340) is lost and the risk of needle (100, 806) piercing the retina (308) is increased. It may therefore be desirable to provide components and algorithms that ensure that the entry bleb is formed by bleb fluid (340) in the subretinal space immediately upon penetration of the choroid (306) by needle (100, 806).

Since linear sensors (660, 876) are configured to track the position of needle (100, 806) in real time, the data from linear sensors (660, 876) may be used to ensure that the entry bleb is formed by bleb fluid (340) in the subretinal space immediately upon penetration of the choroid (306) by needle (806). In particular, whenever linear sensor (660, 876) detects distal advancement of the needle of injector assembly (700) or needle (806), respectively, the corresponding signal sent to control module (500) will automatically trigger delivery of bleb fluid (340). This ensures that bleb fluid (340) will flow out through the distal tip of the needle of injector assembly (700) or needle (806) any time the needle of injector assembly (700) or needle (806) is advanced, on a consistent basis. By ensuring such bleb fluid (340) flow on a consistent basis, system (400) may minimize the risk of accentual perforation of the retina (308).

In the present example, the flow rate of bleb fluid (340) is predetermined. By way of example only, the predetermined flow rate of bleb fluid (340) may be between approximately 100 mL per minute and approximately 300 mL per minute; between approximately 125 mL per minute and approximately 275 mL per minute; between approximately 150 mL per minute and approximately 250 mL per minute; between approximately 175 mL per minute and approximately 225 mL per minute; or approximately 200 mL per minute.

In some other versions, control module (500) provides a user input where the operator may select a desired flow rate for bleb fluid. In addition, or in the alternative, the flow rate for bleb fluid (340) may vary based on the translation speed of needle (100, 806). For instance, if needle (100, 806) is being advanced rapidly, then bleb fluid (340) may be delivered at a relatively high rate; and if needle (100, 806) is being advanced slowly, then bleb fluid (340) may be delivered at a relatively slow rate. In addition, or in the alternative, control module (500) may be configured to provide a very slight delay after linear sensor (660, 876) detects initial advancement of needle (100, 806) before delivering bleb fluid (340). For instance, control module (500) may be configured to wait until needle (100, 806) translates along a predetermined distance (e.g., a distance where needle (100, 806) exits cannula (50, 702, 802)) before delivering bleb fluid (340).

In addition to reducing the risk of needle (100, 806) penetrating the retina (308), the automated delivery of bleb fluid (340) through needle (806) may minimize the risk of the lumen of needle (100, 806) being clogged with small bits of choroid (306) tissue as needle (100, 806) is penetrating the choroid (306).

In addition to providing a basis for control algorithms effecting delivery of bleb fluid (340), data from linear sensors (660, 876) may be used to provide other functionality. For instance, control module (500) may be configured to provide a form of user feedback (e.g., an audible tone, illumination of a light, display of a textual or graphical message, generation of tactile feedback, etc.) to indicate to the operator when needle (100, 806) is in a fully proximal position. This may be important to ensure that needle (100, 806) is fully retracted in cannula (50, 702, 802) when cannula (50, 702, 802) is inserted into the suprachoroidal space. In addition, or in the alternative, control module (500) may be configured to provide a form of user feedback (e.g., an audible tone, illumination of a light, display of a textual or graphical message, generation of tactile feedback, etc.) to indicate to the operator when needle (100, 806) is in a fully distal position. This may prompt the operator to actuate pushbutton (604) or upper rocker plate (830) to thereby initiate delivery of therapeutic agent (341). As yet another merely illustrative example, data from linear sensor (660, 876) may be logged to provide statistical data regarding actual duration of needle (100, 806) extension among various procedures, etc. Other suitable uses for data from linear sensor (660, 876) will be apparent to those of ordinary skill in the art in view of the teachings herein.

As also noted above, therapeutic agent (341) is delivered to the subretinal space after bleb fluid (340) has reached the subretinal space. Both therapeutic agent (341) and bleb fluid (340) are delivered via the same needle (100, 806). In some instances, a small air gap (e.g., approximately 5 µl) is located between therapeutic agent (341) and bleb fluid (340). The term "air," as used herein, should be understood to include any suitable sterile air or gas. When the volume of air between therapeutic agent (341) and bleb fluid (340) reaches the subretinal space (as a bubble or bubbles), the bubble(s) may make it easier to visualize the location of bleb fluid (340), thereby facilitating confirmation that needle (100, 806) has successfully reached the subretinal space. It may therefore be desirable to further enhance the visualization of the location of bleb fluid (340) in the subretinal space. This may be accomplished by providing a combination of bleb fluid (340) and air into needle (100, 806) before introducing therapeutic agent (341) into needle (100, 806).

Figure 36:
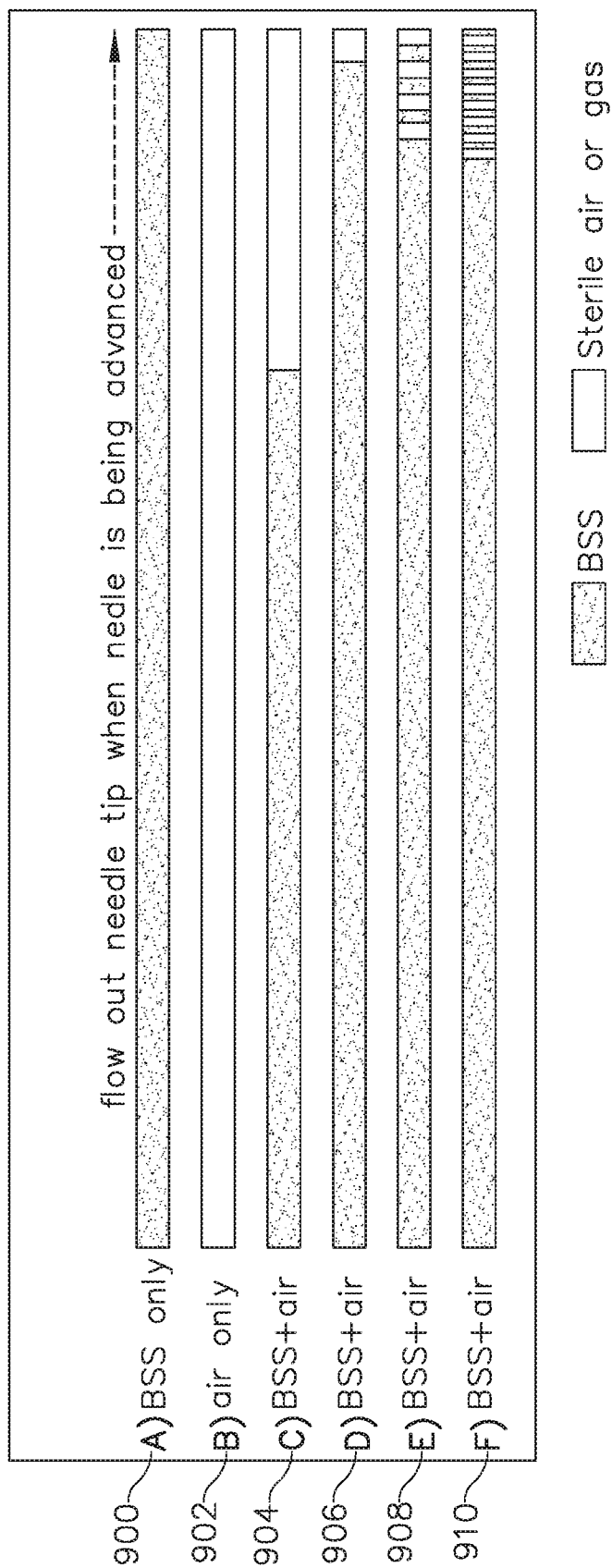
FIG. 36 depicts a diagrammatic view of several exemplary algorithms for delivering a bleb fluid and air into a needle.

FIG. 36 shows various exemplary permutations of the delivery of bleb fluid (340) and air into needle (100, 806) before introducing therapeutic agent (341) into needle (100, 806). For instance, routine (902) provides solely bleb fluid (340) through needle (100, 806) before introducing therapeutic agent (341) into needle (100, 806). Routine (904) provides solely air through needle (100, 806) before introducing therapeutic agent (341) into needle (100, 806). Routine (906) provides an initial volume of bleb fluid (340), followed by air, before introducing therapeutic agent (341) into needle (100, 806). This delayed pocket of air may generate a substantial bubble (or bubbles) that is/are easily visualized it the subretinal space. Routine (908) also provides an initial volume of bleb fluid (340), followed by air, before introducing therapeutic agent (341) into needle (100, 806). This delayed pocket of air is smaller than the pocket of air provided by routine (906). Routine (908) also provides an initial volume of bleb fluid (340), followed by alternating pulses of air and bleb fluid (340), before introducing therapeutic agent (341) into needle (100, 806). The alternating pulses of air and bleb fluid (340), may provide several bubbles that are easily visualized it the subretinal space. Routine (910) also provides an initial volume of bleb fluid (340), followed by alternating pulses of air and bleb fluid (340), before introducing therapeutic agent (341) into needle (100, 806). The alternating pulses of air and bleb fluid (340) in routine (910) are shorter and more numerous than the pulses of air and bleb fluid (340) in routine (908). This may result in a greater number of bubbles, and smaller sized bubbles, in the subretinal space.

In the foregoing examples where air is communicated to needle (100, 806), it may be desirable to use a controlled-pressure system for air delivery rather than a controlled-displacement system. This may account for static cracking pressure and provide an immediate entry bleb of air instead of a delayed entry bleb. In versions where a combination of air and bleb fluid (340) are communicated to needle (100, 806), a valve may be used to alternate between BSS bottle (410) and a source of air. In some variations, the flow rate of bleb fluid (340) may be increased to naturally induce air bubbles in the line. Other suitable components and techniques that may be used to provide a combination of bleb fluid (340) and air through needle (100, 806) will be apparent to those of ordinary skill in the art in view of the teachings herein.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) an injector, wherein the injector comprises: (i) a body, (ii) a flexible cannula extending distally from the body, (iii) a flexible needle, wherein the needle is configured to translate relative to the cannula, and (iv) a sensor, wherein the sensor is operable to detect a position of the needle relative to the cannula; (b) a first fluid conduit coupled with the needle; (c) a second fluid line coupled with the needle; and (d) a control module, wherein the control module is in communication with the sensor, wherein the control module is in communication with the first fluid conduit, wherein the control module is in communication with the second fluid conduit, wherein the control module is configured to provide delivery of a first fluid through the first conduit to the needle based on a signal from the sensor, wherein the control module is further configured to provide delivery of a second fluid through the second conduit to the needle.

Example 2

The apparatus of Example 1, wherein the sensor comprises a linear potentiometer.

Example 3

The apparatus of any one or more of Examples 1 through 2, further comprising a needle actuator, wherein the needle actuator is operable to drive the needle longitudinally relative to the cannula, wherein the sensor is coupled with the linear actuator.

Example 4

The apparatus of any one or more of Examples 1 through 3, wherein the first fluid conduit and the second fluid conduit form a tube set extending between the injector and the control module.

Example 5

The apparatus of any one or more of Examples 1 through 4, wherein the cannula is sized and configured to fit through a sclerotomy formed in a patient's eye.

Example 6

The apparatus of any one or more of Examples 1 through 5, wherein the injector further comprises: (i) an injector subassembly, wherein the body, the cannula, and the needle are part of the injector subassembly, (ii) an injector driver subassembly, wherein the injector driver subassembly comprises a needle driver, and (iii) a flexible driver extending between the injector subassembly and the injector driver subassembly, wherein the flexible driver is configured to communicate motion from the needle driver to the needle to thereby translate the needle relative to the cannula.

Example 7

The apparatus of Example 6, wherein the sensor is contained in the injector driver subassembly.

Example 8

The apparatus of any one or more of Examples 1 through 5, wherein the injector further comprises: (i) a needle driver contained within the body, and (ii) a first user input feature extending from the body, wherein the first user input feature is operable to actuate the needle driver to thereby translate the needle relative to the cannula.

Example 9

The apparatus of Example 8, wherein the first user input feature comprises a rotary knob rotatably coupled with the body.

Example 10

The apparatus of any one or more of Examples 8 through 9, wherein the injector further comprises a second user input feature, wherein the control module is further configured to provide delivery of the second fluid through the second conduit to the needle in response to actuation of the second user input feature.

Example 11

The apparatus of Example 10, wherein the second user input feature comprises a button.

Example 12

The apparatus of any one or more of Examples 10 through 11, wherein the injector further comprises a third user input feature, wherein the control module is further configured to provide delivery of the first fluid through the first conduit to the needle in response to actuation of the third user input feature.

Example 13

The apparatus of any one or more of Examples 1 through 12, wherein the first fluid comprises a liquid.

Example 14

The apparatus of any one or more of Examples 1 through 13, wherein the first fluid comprises a gas.

Example 15

The apparatus of any one or more of Examples 1 through 12, wherein the first fluid comprises a combination of a liquid and a gas.

Example 16

The apparatus of Example 15, wherein the control module is configured to provide delivery of the liquid, followed by delivery of the gas, based on a signal from the sensor.

Example 17

The apparatus of any one or more of Examples 15 through 16, wherein the control module is configured to provide delivery of the liquid, followed by alternating pulses of the gas and the liquid, based on a signal from the sensor.

Example 18

The apparatus of any one or more of Examples 1 through 17, wherein the control module is configured to provide delivery of the first fluid through the first conduit to the needle based on a signal from the sensor indicating that the needle is moving distally relative to the cannula.

Example 19

An apparatus, comprising: (a) an injector, wherein the injector comprises: (i) a body, (ii) a flexible cannula extending distally from the body, (iii) a flexible needle, wherein the needle is configured to translate relative to the cannula, and (iv) a sensor, wherein the sensor is operable to detect a position of the needle relative to the cannula; and (b) a control module, wherein the control module is in communication with the sensor, wherein the control module is configured to provide delivery of a combination of a first liquid and a gas to the needle based on a signal from the sensor, wherein the control module is further configured to provide delivery of a second fluid through the second conduit to the needle after delivering the combination of the first liquid and a gas to the needle.

Example 20

A method comprising: (a) inserting a flexible cannula into a sclerotomy of an eye of a patient, between a sclera and a choroid of the eye; (b) advancing a needle through the cannula while the cannula is disposed between the sclera and the choroid; (c) tracking advancement of the needle with the sensor; (d) automatically dispensing a leading bleb fluid through the needle based on data from the sensor, wherein the act of automatically dispensing a leading bleb fluid is performed while advancing the needle; and (e) injecting a therapeutic agent into a space between a retina and the choroid of the eye, via the advanced needle.

VII. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an injector, wherein the injector comprises:
      (i) a body,
      (ii) a flexible cannula extending distally from the body,
      (iii) a flexible needle, wherein the flexible needle is configured to translate relative to the flexible cannula, and
      (iv) a sensor, wherein the sensor is operable to detect a position of the flexible needle relative to the flexible cannula;
   (b) a first fluid conduit coupled with the flexible needle;
   (c) a second fluid conduit coupled with the flexible needle; and
   (d) a control module, wherein the control module is in communication with the sensor, wherein the control module is in communication with the first fluid conduit, wherein the control module is in communication with the second fluid conduit,
      wherein the control module is configured to provide automated delivery of a first fluid through the first fluid conduit to the flexible needle in response to distal movement of the flexible needle as sensed by the sensor,
      wherein the control module is further configured to provide delivery of a second fluid through the second fluid conduit to the flexible needle.

2. The apparatus of claim 1, wherein the sensor comprises a linear potentiometer.

3. The apparatus of claim 1, further comprising a needle actuator, wherein the needle actuator is operable to drive the flexible needle longitudinally relative to the flexible cannula, wherein the sensor is coupled with the needle actuator.

4. The apparatus of claim 1, wherein the first fluid conduit and the second fluid conduit form a tube set extending between the injector and the control module.

5. The apparatus of claim 1, wherein the flexible cannula is sized and configured to fit through a sclerotomy formed in a patient's eye.

6. The apparatus of claim 1, wherein the injector further comprises:
   (i) an injector subassembly, wherein the body, the flexible cannula, and the flexible needle are part of the injector subassembly, and
   (ii) an injector driver subassembly, wherein the injector driver subassembly comprises a needle driver.

7. The apparatus of claim 6, wherein the sensor is contained in the injector driver subassembly.

8. The apparatus of claim 1, wherein the injector further comprises:
   (i) a needle driver contained within the body, and
   (ii) a first user input feature extending from the body, wherein the first user input feature is operable to actuate the needle driver to thereby translate the flexible needle relative to the flexible cannula.

9. The apparatus of claim 8, wherein the first user input feature comprises a rotary knob rotatably coupled with the body.

10. The apparatus of claim 8, wherein the injector further comprises a second user input feature, wherein the control module is further configured to provide delivery of the second fluid through the second fluid conduit to the flexible needle in response to actuation of the second user input feature.

11. The apparatus of claim 10, wherein the second user input feature comprises a button.

12. The apparatus of claim 10, wherein the control module is further configured to provide automated delivery of the second fluid through the second fluid conduit to the flexible needle in response to actuation of the second user input feature.

13. The apparatus of claim 1, wherein the first fluid comprises a combination of a liquid and a gas.

14. The apparatus of claim 13, wherein the control module is configured to provide delivery of the liquid, followed by delivery of the gas, based on a signal from the sensor.

15. The apparatus of claim 13, wherein the control module is configured to provide delivery of the liquid, followed by alternating pulses of the gas and the liquid, based on a signal from the sensor.

16. The apparatus of claim 1, wherein the control module is configured to provide delivery of the first fluid through the first fluid conduit to the flexible needle based on a signal from the sensor indicating that the flexible needle is moving distally relative to the flexible cannula.

17. An apparatus, comprising:
(a) an injector, wherein the injector comprises:
(i) a body,
(ii) a flexible cannula extending distally from the body,
(iii) a flexible needle, wherein the flexible needle is configured to translate relative to the flexible cannula, and
(iv) a sensor, wherein the sensor is operable to detect a position of the flexible needle relative to the flexible cannula; and
(b) a control module, wherein the control module is in communication with the sensor,
wherein the control module is configured to provide automated delivery of a combination of a first liquid and a gas through a first conduit to the flexible needle in response to distal movement of the flexible needle as sensed by the sensor,
wherein the control module is further configured to provide delivery of a second fluid through a second conduit to the flexible needle after delivering the combination of the first liquid and the gas to the flexible needle.

18. The apparatus of claim 17, further comprising a user input feature, wherein the control module is further configured to provide, in response to actuation of the user input feature, automated delivery of the second fluid through the second fluid conduit to the flexible needle after delivering the combination of the first liquid and the gas to the flexible needle.

19. An apparatus, comprising:
(a) an injector, wherein the injector comprises:
(i) a body,
(ii) a flexible cannula extending distally from the body,
(iii) a flexible needle, wherein the flexible needle is configured to translate relative to the flexible cannula, and
(iv) a sensor, wherein the sensor is operable to detect a position of the flexible needle relative to the flexible cannula;
(b) a first fluid conduit coupled with the flexible needle;
(c) a second fluid conduit coupled with the flexible needle; and
(d) a control module, wherein the control module is in communication with the sensor, wherein the control module is in communication with the first fluid conduit, wherein the control module is in communication with the second fluid conduit,
wherein the control module is configured to provide delivery of a first fluid through the first fluid conduit to the flexible needle based on a signal from the sensor,
wherein the control module is further configured to provide delivery of a second fluid through the second fluid conduit to the flexible needle
wherein the control module is configured to provide at least one of an audible tone, illumination of a light, or generation of tactile feedback to indicate to an operator when the flexible needle is in a fully proximal position or a fully distal position.

* * * * *